United States Patent
Kihara

(10) Patent No.: US 11,565,240 B2
(45) Date of Patent: Jan. 31, 2023

(54) MIXED MODE AFFINITY CHROMATOGRAPHY CARRIER

(71) Applicant: FUJIFILM Corporation, Tokyo (JP)

(72) Inventor: Shiori Kihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 891 days.

(21) Appl. No.: 16/402,447

(22) Filed: May 3, 2019

(65) Prior Publication Data

US 2019/0247827 A1 Aug. 15, 2019

Related U.S. Application Data

(63) Continuation of application No. PCT/JP2017/033642, filed on Sep. 19, 2017.

(30) Foreign Application Priority Data

Dec. 9, 2016 (JP) .............................. JP2016-239536

(51) Int. Cl.
*B01J 20/286* (2006.01)
*C07K 16/00* (2006.01)
*C07K 1/22* (2006.01)
*B01D 15/30* (2006.01)
*B01D 15/38* (2006.01)
*B01D 15/36* (2006.01)
*C07K 1/16* (2006.01)
*B01J 20/281* (2006.01)
*C07K 7/64* (2006.01)
*C07K 7/50* (2006.01)

(52) U.S. Cl.
CPC .......... *B01J 20/286* (2013.01); *B01D 15/305* (2013.01); *B01D 15/36* (2013.01); *B01D 15/362* (2013.01); *B01D 15/38* (2013.01); *B01D 15/3809* (2013.01); *B01J 20/281* (2013.01); *C07K 1/165* (2013.01); *C07K 1/22* (2013.01); *C07K 7/50* (2013.01); *C07K 7/64* (2013.01); *C07K 16/00* (2013.01)

(58) Field of Classification Search
CPC ........ B01J 20/286; B01J 28/01; B01J 20/321; B01J 20/3212; B01J 20/3274; B01J 20/3285; B01J 39/26; B01D 15/305; B01D 15/36; B01D 15/362; B01D 15/38; B01D 15/3809; B01D 15/3847; C07K 1/165; C07K 1/22; C07K 7/50; C07K 7/64; C07K 16/00; C07K 16/065; C07K 17/12; C07K 17/08; C07K 2317/14
See application file for complete search history.

(56) References Cited

U.S. PATENT DOCUMENTS

| 5,241,047 A | 8/1993 | Lacroix | |
|---|---|---|---|
| 2008/0237124 A1* | 10/2008 | Axen | B01J 20/289 252/184 |
| 2011/0044987 A1* | 2/2011 | Hofbauer | A61P 35/00 424/139.1 |
| 2014/0274790 A1* | 9/2014 | Ito | C07K 17/06 536/23.1 |
| 2014/0335089 A1* | 11/2014 | Igawa | C07K 16/283 435/69.6 |
| 2015/0044701 A1* | 2/2015 | Ito | C07K 16/065 536/23.1 |
| 2015/0078999 A1* | 3/2015 | Heath | A61K 49/0041 435/7.1 |
| 2015/0080549 A1* | 3/2015 | Kariyuki | C07K 7/06 530/321 |
| 2015/0225445 A1* | 8/2015 | Minakuchi | B01J 39/26 530/402 |
| 2018/0229215 A1 | 8/2018 | Kihara | |

FOREIGN PATENT DOCUMENTS

| CN | 101252986 A | 8/2008 |
|---|---|---|
| CN | 103890174 A | 6/2014 |
| CN | 104603144 A | 5/2015 |
| EP | 2749646 A1 | 7/2014 |
| EP | 2787079 A1 | 10/2014 |
| EP | 2894159 A1 | 7/2015 |
| JP | 2010-133734 A | 6/2010 |
| JP | 2013-088398 A | 5/2013 |
| JP | 2016-069329 A | 5/2016 |
| WO | 92/00997 A1 | 1/1992 |
| WO | 2007/027139 A1 | 3/2007 |
| WO | 2013/027796 A1 | 2/2013 |
| WO | 2013/081037 A1 | 6/2013 |
| WO | 2014/010813 A1 | 1/2014 |
| WO | 2014/034457 A1 | 3/2014 |
| WO | 2017/069254 A1 | 4/2017 |
| WO | 2017/069269 A1 | 4/2017 |

OTHER PUBLICATIONS

Office Action dated Jan. 28, 2022 in Chinese Application No. 201780070910.9.
Communication dated May 26, 2020 by the Japanese Patent Office in application No. 2018-554831.
International Preliminary Report on Patentability dated Jun. 11, 2019 from the International Bureau in counterpart International Application No. PCT/JP2017/033642.
International Search Report dated Dec. 19, 2017 from the International Searching Authority in counterpart International Application No. PCT/JP2017/033642.
Written Opinion dated Dec. 19, 2017 from the International Bureau in counterpart International Application No. PCT/JP2017/033642.
Communication dated Dec. 1, 2020, issued by the Japanese Patent Office in application No. 2018-554831.

(Continued)

*Primary Examiner* — Emmanuel E Duke

(74) *Attorney, Agent, or Firm* — Sughrue Mion, PLLC

(57) ABSTRACT

A mixed mode affinity chromatography carrier includes a substrate, a hydrophilic polymer, an antibody-binding cyclic peptide, and a cation exchange group.

18 Claims, No Drawings
Specification includes a Sequence Listing.

(56) References Cited

OTHER PUBLICATIONS

Extended European Search Report dated Dec. 5, 2019 issued by the European Patent Office in counterpart application No. 17879511.8.
Communication dated Sep. 1, 2020, from the Canadian Intellectual Property Office in application No. CA3044645.

* cited by examiner

US 11,565,240 B2

MIXED MODE AFFINITY CHROMATOGRAPHY CARRIER

CROSS-REFERENCE TO RELATED APPLICATIONS

This application is a Continuation of PCT International Application No. PCT/JP2017/033642, filed on Sep. 19, 2017, which claims priority under 35 U.S.C. § 119(a) to Japanese Patent Application No. 2016-239536, filed on Dec. 9, 2016. Each of the above application(s) is hereby expressly incorporated by reference, in its entirety, into the present application.

BACKGROUND OF THE INVENTION

1. Field of the Invention

The present invention relates to a mixed mode affinity chromatography carrier.

2. Description of the Related Art

In recent years, along with the development of genetic engineering, protein engineering and cell engineering, development of drug utilizing functions of an antibody, which is called an antibody drug, has been actively conducted. As compared with a drug in the related art, an antibody drug works more specifically on a target molecule, and it is therefore expected that use of an antibody drug will result in further reduced side effects and high therapeutic effects. In fact, an antibody drug contributes to improvements of various pathological conditions.

Meanwhile, since an antibody drug is administered to a living body in large amounts, the purity has a large influence on the quality of the antibody drug in the case of comparing with other recombinant protein drugs. Since an antibody drug is produced by purifying antibodies expressed in a host cell by genetic recombination, incorporation of impurities derived from host cells and production processes poses a problem. For example, since a host cell protein (HCP) remaining as an impurity in an antibody drug is assumed to be associated with the onset of anaphylaxis upon administration of the antibody drug, it is required that purification purity is improved to reduce impurities.

For example, WO2014/034457A discloses a mixed mode antibody affinity separation matrix having an antibody affinity ligand and a cation exchange group on the same separation matrix (Claim 1). Further, it is disclosed that the antibody affinity ligand is at least one selected from protein A, protein G, protein L, protein H, protein D, protein Arp, protein FcγR, an antibody binding synthetic ligand, or analogous substances thereof (Claim 5).

In addition, for example, JP2016-069329A discloses a mixed mode carrier having a group including an acid group and an affinity ligand on a synthetic polymer carrier (Claim 11). Further, as the antibody affinity ligand, protein A, protein G, protein L, protein H, protein D, protein Arp, protein FcγR, an antibody binding synthetic peptide ligand, and analogous substances thereof are described (<0043>).

In addition, for example, JP2013-088398A discloses a separating agent obtained by introducing an interactive functional group into a surface-modified porous crosslinking particle (<0011>). In addition, it is disclosed that as the interactive functional group, an ion exchange group; an affinity ligand; and a hydrophobic group such as an alkyl group, a phenyl group, and a polyalkyl ether group are preferable, and that the separating agent obtained by introducing such an interactive functional group can be effectively used especially as an adsorbent of a polymer substance such as protein, particularly as a chromatography separating agent (<0026>).

SUMMARY OF THE INVENTION

Currently, purification of an antibody drug is generally carried out by affinity chromatography using protein A as an affinity ligand. However, the protein A is a protein derived from *Staphylococcus aureus* and has high immunogenicity to a human body. Therefore, in a case where the protein A is administered to a human body after being mixed in a purified antibody, the protein A may cause unexpected immune response. In addition, since the protein A is produced by a genetic engineering method using *Escherichia coli*, there is a concern that lipopolysaccharide (LPS; lipid A) which is an *E. coli*-derived endotoxin is mixed in the purified antibody. For this reason, the protein A is required to have a high degree of purification, which is one of the factors that increase antibody purification costs.

The present inventors have conceived of using an antibody binding peptide that can be produced at a lower cost than that of the protein A as the affinity ligand used in a mixed mode affinity chromatography carrier and have examined antibody adsorption capacity, impurities removal function, and drug resistance.

As a result, the present inventors have found that there is room for improvement in one or more of antibody adsorption capacity, impurities removal function, and drug resistance in a mixed mode affinity chromatography carrier using a straight chain peptide as an affinity ligand. For example, although a straight chain peptide is used as the affinity ligand in Comparative Example 2 to be described later, it is shown that antibody adsorption capacity and drug resistance are insufficient and required to be improved.

An object of the present invention is to provide a mixed mode affinity chromatography carrier excellent in all of antibody adsorption capacity, impurities removal function, and drug resistance.

As a result of intensive examination in order to achieve the object, the present inventors have found that a mixed mode affinity chromatography carrier including a substrate, a hydrophilic polymer, a cyclic peptide, and a cation exchange group is excellent in all of antibody adsorption capacity, impurities removal function, and drug resistance, thereby completing the present invention.

That is, the present invention provides the following [1] to [21].

[1] A mixed mode affinity chromatography carrier, comprising: a substrate; a hydrophilic polymer; an antibody-binding cyclic peptide; and a cation exchange group.
  [2] The mixed mode affinity chromatography carrier according to [1], in which the antibody-binding cyclic peptide includes a cyclic portion cyclized by intramolecular crosslinking between side chains.
  [3] The mixed mode affinity chromatography carrier according to [2], in which the intramolecular crosslinking includes at least one selected from the group consisting of a disulfide bond, a thioether bond, a triazole bond, and an amide bond.
  [4] The mixed mode affinity chromatography carrier according to [2] or [3], in which the intramolecular crosslinking includes at least one selected from the group consisting of a disulfide bond, a thioether bond, and a triazole bond.

[5] The mixed mode affinity chromatography carrier according to [4], in which the disulfide bond is a disulfide bond formed between a side chain thiol group of a first amino acid residue derived from an amino acid having a thiol group in a side chain other than L-cysteine and D-cysteine and a side chain thiol group of a second amino acid residue derived from an amino acid having a thiol group in a side chain other than L-cysteine and D-cysteine, and in which the thioether bond is a thioether bond formed between a side chain thiol group of a first amino acid residue derived from an amino acid having a thiol group in a side chain other than L-cysteine and D-cysteine and a side chain haloacetyl group of a second amino acid residue derived from an amino acid having a haloacetyl group in a side chain.

[6] The mixed mode affinity chromatography carrier according to [4], in which the disulfide bond is a disulfide bond formed between a side chain thiol group of a first amino acid residue derived from an amino acid having a thiol group in a side chain selected from the group consisting of cysteine, homocysteine, and penicillamine and a side chain thiol group of a second amino acid residue derived from an amino acid having a thiol group in a side chain selected from the group consisting of cysteine, homocysteine, and penicillamine, and in which the thioether bond is a thioether bond formed between a side chain thiol group of a first amino acid residue derived from an amino acid having a thiol group in a side chain selected from the group consisting of cysteine, homocysteine, and penicillamine and a side chain haloacetyl group of a second amino acid residue derived from an amino acid having a haloacetyl group in a side chain.

[7] The mixed mode affinity chromatography carrier according to any one of [4] to [6], in which the disulfide bond is a disulfide bond formed between a side chain thiol group of a first amino acid residue derived from an amino acid having a thiol group in a side chain selected from the group consisting of homocysteine and penicillamine and the side chain thiol group of a second amino acid residue derived from an amino acid having a thiol group in a side chain selected from the group consisting of homocysteine and penicillamine, and in which the thioether bond is a thioether bond formed between a side chain thiol group of a first amino acid residue derived from an amino acid having a thiol group in a side chain selected from the group consisting of homocysteine and penicillamine and the side chain haloacetyl group of a second amino acid residue derived from an amino acid having a haloacetyl group in a side chain.

[8] The mixed mode affinity chromatography carrier according to [2] or [4], in which the intramolecular crosslinking is a disulfide bond formed between a side chain thiol group of a first amino acid residue derived from an amino acid having a thiol group in a side chain selected from the group consisting of homocysteine and penicillamine and a side chain thiol group of a second amino acid residue derived from an amino acid having a thiol group in a side chain selected from the group consisting of homocysteine and penicillamine, or a thioether bond formed between a side chain thiol group of a first amino acid residue derived from an amino acid having a thiol group in a side chain selected from the group consisting of homocysteine and penicillamine and a side chain haloacetyl group of a second amino acid residue derived from an amino acid having a haloacetyl group in a side chain.

[9] The mixed mode affinity chromatography carrier according to [8], in which the disulfide bond is a disulfide bond formed between a side chain thiol group of a first amino acid residue derived from homocysteine and a side chain thiol group of a second amino acid residue derived from homocysteine, and in which the thioether bond is a thioether bond formed between a side chain thiol group of a first amino acid residue derived from homocysteine and a side chain haloacetyl group of a second amino acid residue derived from an amino acid having a haloacetyl group in a side chain.

[10] The mixed mode affinity chromatography carrier according to any one of [2] to [9], in which the number of the amino acid residues of the cyclic portion is 8 to 14.

[11] The mixed mode affinity chromatography carrier according to any one of [1] to [10], in which the antibody-binding cyclic peptide includes a straight chain portion.

[12] The mixed mode affinity chromatography carrier according to [11], in which the straight chain portion includes an amino acid residue having at least one selected from the group consisting of a hydroxy group and a carboxy group in a side chain.

[13] The mixed mode affinity chromatography carrier according to any one of [1] to [12], in which the substrate is at least one selected from the group consisting of a polysaccharide, an acrylate-based polymer, a methacrylate-based polymer, and a styrene-based polymer.

[14] The mixed mode affinity chromatography carrier according to any one of [1] to [13], in which the substrate is at least one selected from the group consisting of a polysaccharide, an acrylate-based polymer, and a methacrylate-based polymer.

[15] The mixed mode affinity chromatography carrier according to any one of [1] to [14], in which the substrate is at least one selected from the group consisting of agarose and cellulose.

[16] The mixed mode affinity chromatography carrier according to any one of [1] to [15], in which the hydrophilic polymer is a hydrophilic polysaccharide.

[17] The mixed mode affinity chromatography carrier according to [16], in which the hydrophilic polysaccharide is at least one selected from the group consisting of dextran, carboxymethyl dextran, pullulan, hydroxyethyl cellulose, and carboxymethyl cellulose.

[18] The mixed mode affinity chromatography carrier according to [16] or [17], in which the hydrophilic polysaccharide is at least one selected from the group consisting of dextran, carboxymethyl dextran, and pullulan.

[19] The mixed mode affinity chromatography carrier according to any one of [1] to [18], in which a molecular weight of the antibody-binding cyclic peptide is less than 5,000.

[20] The mixed mode affinity chromatography carrier according to any one of [1] to [19], in which the cation exchange group is a carboxy group or a sulfoxy group.

[21] The mixed mode affinity chromatography carrier according to any one of [1] to [20], in which the cation exchange group is a carboxy group.

According to the present invention, it is possible to provide a mixed mode affinity chromatography carrier excellent in all of antibody adsorption capacity, impurities removal function, and drug resistance.

DESCRIPTION OF THE PREFERRED EMBODIMENTS

Hereinafter, the mixed mode affinity chromatography carrier of the present invention and the production method thereof will be described in detail.

In the present invention, with respect to a numerical range, numerical values on the left and right of "to" are intended to be included in the numerical range.

[Mixed Mode Affinity Chromatography Carrier]

The mixed mode affinity chromatography carrier according to the embodiment of the invention includes a substrate, a hydrophilic polymer, an antibody-binding cyclic peptide, and a cation exchange group.

Since the mixed mode affinity chromatography carrier of the present invention has such a configuration, it is considered that in a case of being applied to antibody purifying affinity chromatography, the mixed mode affinity chromatography carrier is excellent in all of antibody adsorption capacity, impurities removal function, and drug resistance. The reason is not limited but is assumed to be as follows.

By having the antibody-binding cyclic peptide and the cation exchange group in the same carrier, ligands of both the antibody-binding cyclic peptide and the cation exchange group cooperatively act. Thus, with specific adsorption function and aggregate removal function, the mixed mode affinity chromatography carrier became excellent in all of antibody adsorption capacity, impurities removal function, and drug resistance.

In the present invention, the impurities removal function is a HCP purification factor [HCP amount before purification (ppm)/HCP amount after purification (ppm)] which is a ratio of the HCP amount before purification (ppm) and the HCP amount after purification (ppm), and is a measure of impurities removal function of a chromatography carrier.

<Substrate>

The substrate used in the mixed mode affinity chromatography carrier of the present invention is not particularly limited, but is preferably at least one selected from the group consisting of a polysaccharide, an acrylate-based polymer, a methacrylate-based polymer, and a styrene-based polymer, more preferably at least one selected from the group consisting of a polysaccharide, an acrylate-based polymer, a methacrylate-based polymer, and still more preferably at least one selected from the group consisting of agarose and cellulose.

One substrate may be used alone or two or more substrates may be used in combination.

<<Polysaccharide>>

The polysaccharide is not particularly limited, and examples thereof include natural polysaccharides such as cellulose, agarose, dextran, chitosan, and glucomannan, and crosslinked polysaccharides obtained by introducing a crosslinked structure into these natural polysaccharides. The crosslinked polysaccharide can be produced, for example, by introducing a crosslinked structure into the hydroxyl group of the natural polysaccharide using a crosslinking agent such as epichlorohydrin, (poly)alkylene glycol diglycidyl ether, and alkylene diisocyanate.

The polysaccharide is preferably at least one selected from cellulose, crosslinked cellulose, agarose or crosslinked agarose, and more preferably at least one selected from agarose or crosslinked agarose.

<<Acrylate-Based Polymer>>

The acrylate-based polymer is not particularly limited, and examples thereof include a polymer obtained by polymerizing one kind of acrylic acid esters such as methyl acrylate, ethyl acrylate, hydroxyethyl acrylate, hydroxypropyl acrylate, butyl acrylate, stearyl acrylate, 2-ethylhexyl acrylate, cyclohexyl acrylate, glycerin monoacrylate, glycidyl acrylate, 4,5-epoxybutyl acrylate, and 9,10-epoxy stearyl acrylate; a copolymer obtained by copolymerizing two or more kinds of acrylic acid esters; and a copolymer obtained by copolymerizing one or more kinds of acrylic acid esters with one or more kinds of vinyl group-containing compounds other than acrylic acid esters. Examples of vinyl group-containing compounds other than acrylic acid esters include a monovinyl compound such as ethylene or propylene, an aromatic polyvinyl compound such as divinylbenzene or trivinylbenzene, and a polyvinyl compound such as butadiene, methylenebisacrylamide, or triallyl isocyanurate. A crosslinked structure may be introduced into these polymers or copolymers using a crosslinking agent such as epichlorohydrin, (poly)alkylene glycol diglycidyl ether, or alkylene diisocyanate.

<<Methacrylate-Based Polymer>>

The methacrylate-based polymer is not particularly limited, and examples thereof include a polymer obtained by polymerizing one kind of methacrylic acid esters such as methyl methacrylate, ethyl methacrylate, hydroxyethyl methacrylate, hydroxypropyl methacrylate, butyl methacrylate, stearyl methacrylate, 2-ethylhexyl methacrylate, cyclohexyl methacrylate, glycerin monomethacrylate, glycidyl methacrylate, 4,5-epoxybutyl methacrylate, and 9,10-epoxy stearyl methacrylate; a copolymer obtained by copolymerizing two or more kinds of methacrylic acid esters; and a copolymer obtained by copolymerizing one or more kinds of methacrylic acid esters with one or more kinds of vinyl group-containing compounds other than methacrylic acid esters. Examples of the vinyl group-containing compounds other than methacrylic acid esters include a compound exemplified a vinyl group-containing compound other than the acrylic acid esters. A crosslinked structure may be introduced into these polymers or copolymers using the crosslinking agent used in the acrylate-based polymer.

<<Styrene-Based Polymer>>

The styrene-based polymer is not particularly limited, and examples thereof include a polymer obtained by polymerizing one kind of styrene-based compounds such as styrene, methylstyrene, ethylstyrene, hydroxystyrene, and chlorostyrene; a copolymer obtained by polymerizing two or more kinds of styrene-based compounds; and a copolymer obtained by copolymerizing one or more kinds of styrene-based compounds with one or more kinds of vinyl group-containing compounds other than styrene-based compounds. Examples of vinyl group-containing compounds other than styrene-based compounds include a compound exemplified as vinyl group-containing compounds other than the acrylic acid esters. A crosslinked structure may be introduced into these polymers or copolymers using a crosslinking agent used in the acrylate-based polymer.

<<Structure of Substrate>>

The substrate is preferably a porous particle or a porous film. Since the substrate is a porous particle or a porous film, the surface area thereof is increased and therefore the treatment capacity per unit time can be increased.

(Pore Volume)

Although the pore volume of the substrate in the case where the substrate is a porous particle or a porous film is not particularly limited, the pore volume measured by a mercury porosimeter is preferably within the range of 0.2 mL/g to 10 mL/g and more preferably 0.2 mL/g to 5.0 mL/g. In the case where the pore volume is within this range, the antibody adsorption capacity is improved. In addition, the mechanical strength does not decrease.

(Specific Surface Area)

Although the specific surface area of the substrate in the case where the substrate is a porous particle or a porous film is not particularly limited, the specific surface area measured by a Brunauer, Emmett, Teller (BET) method (BET specific surface area) is preferably within the range of 2 m²/g to 1,500 m²/g and more preferably 5 m²/g to 1,000 m²/g. In the case where the specific surface area is within this range, the antibody adsorption capacity is improved.

(Average Particle Diameter)

The average particle diameter of the substrate in the case where the substrate is a porous particle is not particularly limited, but it is preferably within the range of 0.5 μm to 1,000 μm, more preferably 1 μm to 250 μm, and still more preferably 2 μm to 150 μm. In the case where the average particle diameter is within this range, the loss of pressure in the case of a column being filled with porous particles and then allowing a liquid to pass therethrough can be decreased and the flow rate of the liquid can be increased, which, in turn, results in an improved treatment efficiency as well as improved antibody adsorption capacity. The average particle diameter of the porous particles can be measured by a known method. For example, an average particle diameter can be obtained by measuring particle diameters of 100 or more porous particles by an optical microscope and calculating the median diameter from the particle diameter distribution thereof.

<<Specific Examples of Substrate>>

Specific examples of the substrate include, but are not limited to, commercially available products such as SEPHAROSE series (manufactured by GE Healthcare GmbH) which is an agarose-based carrier ("SEPHAROSE" is a registered trademark), CELLUFINE series (manufactured by JNC Corporation) which is a cellulose-based crosslinking carrier ("CELLUFINE" is a registered trademark), SEPHACRYL series (manufactured by GE Healthcare GmbH) which is a crosslinked polymer of allyl dextran and N,N'-methylenebisacrylamide ("SEPHACRYL" is a registered trademark), and TOYOPEARL HW series (manufactured by Tosoh Corporation) which is an acrylate-based carrier ("TOYOPEARL" is a registered trademark).

In addition, as a commercially available substrate, a substrate obtained by introducing a functional group capable of being covalently bonded to a hydroxy group such as epoxy group may be used. For example, it is possible to use a carrier obtained by treating an agarose-based carrier with 2-chloromethyloxirane (synonym: epichlorohydrin), glycidylating a hydroxy group of agarose, and introducing an epoxy group into a surface thereof.

<Hydrophilic Polymer>

Coating the substrate with a hydrophilic polymer increases the hydrophilicity of the surface of the mixed mode affinity chromatography carrier of the present invention and suppresses adsorption of non-specific adsorbates, which thus has an effect of improving the purification purity.

The hydrophilic polymer used in the mixed mode affinity chromatography carrier of the present invention is not particularly limited, and is preferably at least one selected from the group consisting of hydrophilic polysaccharides, more preferably at least one selected from the group consisting of dextran, carboxymethyl dextran, pullulan, hydroxyethyl cellulose, and carboxymethyl cellulose, and still more preferably at least one selected from the group consisting of dextran, carboxymethyl dextran, and pullulan.

One hydrophilic polymer may be used alone or two or more hydrophilic polymers may be used in combination.

In addition, the hydrophilic polymer is preferably immobilized to the substrate by a covalent bond.

In a case where the substrate is a porous particle, the hydrophilic polymer preferably has a functional group covalently binding to a hydroxy group on a surface thereof. Examples of the functional group covalently binding to a hydroxy group include a reactive functional group such as an epoxy group and a glycidyl group; a hydroxy group activated by cyanogen bromide, N,N-disuccinimidyl carbonate (DSC), and the like; an aldehyde group (formyl group); and an activated carboxylic acid group such as N-hydroxy succinimide ester and carbonyl diimidazole activated ester.

<<Hydrophilic Polysaccharide>>

The hydrophilic polysaccharide is not particularly limited, but it is preferably at least one selected from dextran, carboxymethyl dextran and pullulan and more preferably dextran, from the viewpoint of having a high effect of improving the purification purity.

<<Molecular Weight of Hydrophilic Polymer>>

The molecular weight of the hydrophilic polymer is not particularly limited, but it is preferably within the range of 0.10 dL/g or more, more preferably 0.10 dL/g to 0.90 dL/g, still more preferably 0.12 dL/g to 0.40 dL/g, even more preferably 0.15 dL/g to 0.30 dL/g, and even still more preferably 0.15 dL/g to 0.25 dL/g in terms of intrinsic viscosity. In a case where the intrinsic viscosity is within the range, the purification purity is further improved. The intrinsic viscosity can be determined by measuring the viscosity of polymer solutions of several different concentrations according to the viscosity measurement method in the general measurement method listed in the 16th revised Japanese Pharmacopoeia, the first method "capillary viscometer method" to measure the concentration dependence of the viscosity, and extrapolating the concentration of the obtained straight line to 0.

(Intrinsic Viscosity)

Meanwhile, the following Mark-Houwink-Sakurada equation is established between the intrinsic viscosity t and the molecular weight M of the polymer. Therefore, once the molecular weight of several samples is determined by using a direct measurement method, and K and a are determined from the molecular weight and the respective intrinsic viscosity values, the molecular weight M is determined by measuring the intrinsic viscosity q and the intrinsic viscosity q is determined by measuring the molecular weight M, respectively, for the same type of polymers.

$$\eta = KM^\alpha$$

where K and α are constants determined by the type of polymer, the type of solvent and the temperature.

For example, it is known that the intrinsic viscosity ($\eta_{Dextran}$) and the weight-average molecular weight ($Mw_{Dextran}$) of dextran satisfy the following relational expression.

$$\eta_{Dextran}[dL/g] = 9 \times 10^{-4} \times Mw_{Dextran}^{0.5}[dL/g]$$

<<Coating Amount of Hydrophilic Polymer>>

The coating amount of the hydrophilic polymer (hereinafter, sometimes simply referred to as "hydrophilic polymer coating amount") is not particularly limited, but it is preferably 3 mg/g-dry gel to 450 mg/g-dry gel, more preferably 3 mg/g-dry gel to 250 mg/g-dry gel, still more preferably 3 mg/g-dry gel to 230 mg/g-dry gel, even more preferably 10 mg/g-dry gel to 230 mg/g-dry gel, and even more preferably 20 mg/g-dry gel to 230 mg/g-dry gel.

In the case where the hydrophilic polymer coating amount is within this range, the hydrophilicity of the surface of the mixed mode affinity chromatography carrier of the present invention is moderately increased to thereby suppress adsorption of non-specific adsorbates and there is room for diffusion and penetration of antibodies into a substrate, thus increasing an antibody adsorption capacity, so that the purification purity is further improved and the purification cost is decreased. The hydrophilic polymer does not need to cover the entire surface of the substrate, and it is sufficient that the hydrophilic polymer covers at least a part of the substrate.

The hydrophilic polymer coating amount [unit: mg/g-dry gel] is calculated by dividing the dry weight ($W_P$) [unit: mg] of the coated hydrophilic polymer by the dry weight ($W_0$) [unit: g-dry gel] of the substrate before coating. The dry weight ($W_P$) of the hydrophilic polymer is the difference ($W_1 - W_0$) [unit: mg] between the dry weight ($W_1$) of the total amount of the carrier and the dry weight ($W_0$) of the substrate before coating.

Therefore, the hydrophilic polymer coating amount can be determined by the following equation.

$$\text{Hydrophilic polymer coating amount (mg/g-dry gel)} = W_P/W_0 = (W_1 - W_0)/W_0$$

The dry weight ($W_0$) of the substrate before coating can be calculated as follows.

$$W_0 = W_{0,xg} \times w_0 / x$$

in which $W_{0,xg}$: dry weight of wet gel xg of substrate before coating, $w_0$: wet gel weight of substrate before coating used for hydrophilic polymer coating reaction, and x: wet gel weight (xg) of substrate before coating used for drying.

The dry weight ($W_1$) of the total amount of the carrier can also be calculated in the same manner.

An example of the measurement method of the hydrophilic polymer coating amount is described.

First, 5 g of wet gel of the substrate before coating is reduced-pressure dried until there is no change in the weight at 50° C. to measure the weight, and the dry weight of the substrate before coating is obtained from a product with the wet gel weight of the substrate before coating used in the hydrophilic polymer coating reaction.

Next, 5 g of wet gel of the carrier obtained by coating the hydrophilic polymer on the substrate before coating is reduced-pressure dried until there is no change in the weight at 50° C. to measure the weight, and the dry weight of the carrier is obtained from a product with the wet gel weight of the carrier obtained after the hydrophilic polymer coating reaction.

Furthermore, a difference between the dry weight of the carrier and the dry weight of the substrate before coating is obtained as the dry weight of the hydrophilic polymer which coats the substrate before coating.

Lastly, the hydrophilic polymer coating amount is calculated as the dry weight of the hydrophilic polymer per the dry weight of the substrate before coating.

(Hydrophilicity)

In the present invention, hydrophilicity of the polymer or the polysaccharide means that the polymer of the polysaccharide includes at least one hydrophilic group. Examples of the hydrophilic group preferably include functional groups such as a carboxy group, an alkali metal salt of a carboxy group, a sulfonic acid group, an alkali metal salt of a sulfonic acid group, a hydroxy group, an amide group, a carbamoyl group, a sulfonamide group, a sulfamoyl group, a phosphate group, an alkali metal salt of a phosphate group, an oxyphosphate group, and an alkali metal salt of an oxyphosphate group. These hydrophilic group may exist at a position in a polymer, for example, may bind to a polymer main chain terminal and/or side chain directly or via a linking group. In addition, the hydrophilic group exists in one molecule, preferably in the plurality of numbers.

<Antibody-Binding Cyclic Peptide>

The antibody-binding cyclic peptide used in the mixed mode affinity chromatography carrier of the present invention is not particularly limited, but preferably has a cyclic portion cyclized by an intramolecular crosslinking between side chains.

The intramolecular crosslinking includes preferably at least one selected from the group consisting of a disulfide bond, a thioether bond, a triazole bond, and an amide bond, more preferably at least one selected from the group consisting of a disulfide bond, a thioether bond, and a triazole bond, and still more preferably a disulfide bond or a thioether bond.

In the present specification, the antibody-binding cyclic peptide is sometimes simply referred to as "cyclic peptide" or "affinity ligand".

<<Disulfide Bond>>

The disulfide bond is not particularly limited as long as the disulfide bond is an "S—S" bond, and examples of the disulfide bond include an S—S bond formed between two thiol groups (referred to as "mercapto group").

(1) The disulfide bond is preferably a disulfide bond formed between a side chain thiol group of a first amino acid residue derived from an amino acid having a thiol group in a side chain and a side chain thiol group of a second amino acid residue derived from an amino acid having a thiol group in a side chain.

(2a) The disulfide bond is more preferably a disulfide bond formed between a side chain thiol group of a first amino acid residue derived from an amino acid having a thiol group in a side chain other than L-cysteine and D-cysteine and a side chain thiol group of a second amino acid residue derived from an amino acid having a thiol group in a side chain other than L-cysteine and D-cysteine.

(2b) The disulfide bond is more preferably a disulfide bond formed between a side chain thiol group of a first amino acid residue derived from an amino acid having a thiol group in a side chain selected from the group consisting of cysteine, homocysteine, penicillamine and a side chain thiol group of a second amino acid residue derived from an amino acid having a thiol group in a side chain selected from the group consisting of cysteine, homocysteine, and penicillamine.

Examples of such a disulfide bond include that represented by the following formula.

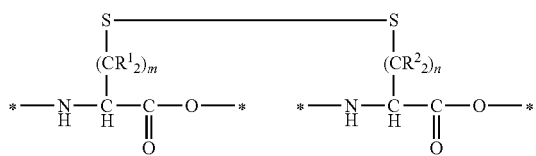

In the formula:
m and n are each independently 1 or 2;
in a case where m=1, $R^1$ is a hydrogen atom or a methyl group;
in a case where m=2, $R^1$ is a hydrogen atom;
in a case where n=1, $R^2$ is a hydrogen atom or a methyl group;
in a case where n=2, $R^2$ is a hydrogen atom; and
* represents a coupling point with other amino acid residues or other substituents.

(3) The disulfide bond is more preferably a disulfide bond formed between a side chain thiol group of a first amino acid residue derived from an amino acid having a thiol group in a side chain selected from the group consisting of homocysteine and penicillamine and a side chain thiol group of a second amino acid residue derived from an amino acid having a thiol group in a side chain selected from the group consisting of homocysteine and penicillamine.

Examples of such a disulfide bond include that represented by the following formula.

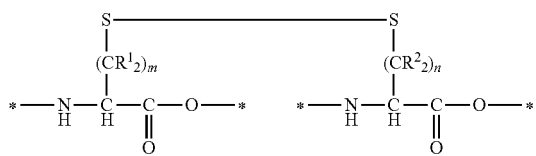

In the formula:
m and n are each independently 1 or 2;
in a case where m=1, $R^1$ is a methyl group;
in a case where m=2, $R^1$ is a hydrogen atom;
in a case where n=1, $R^2$ is a methyl group;
in a case where n=2, $R^2$ is a hydrogen atom; and
* represents a coupling point with other amino acid residues or other substituents.

(4) The disulfide bond is even more preferably a disulfide bond formed between a side chain thiol group of a first amino acid residue derived from homocysteine and a side chain thiol group of a second amino acid residue derived from homocysteine.

Examples of such a disulfide bond include that represented by the following formula.

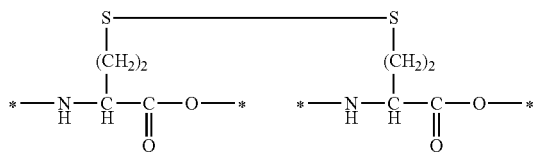

In the formula, * represents a coupling point with other amino acid residues or other substituents.
(Particularly Preferable Disulfide Bond)
Since the disulfide bond has high alkali resistance, the mixed mode affinity chromatography carrier maintains antibody binding properties even if washing is repetitively performed by alkali, and thus it is possible to decrease the antibody purification cost. Such a disulfide bond is preferably a disulfide bond other than disulfide bonds formed between two cysteine residues, more preferably a disulfide bond formed between amino acid residues derived from an amino acid having a thiol group in a side chain other than cysteine, and particularly preferably a disulfide bond formed between two homocysteine residues.

<<Thioether Bond>>

The thioether bond is not particularly limited as long as the thioether bond is an "—S—" bond in the form of substituting an oxygen atom of the ether bond "—O—" with a sulfur atom, and examples thereof include a —S— bond formed between a thiol group (referred to as "mercapto group") and a haloacetyl group, where the haloacetyl group is preferably a chloroacetyl group or a bromoacetyl group, and more preferably a chloroacetyl group. In addition, the haloacetyl group is preferably a group introduced into an amino acid in the form of substituting a hydrogen atom of a side chain amino group.

Examples of the amino acid having a haloacetyl group in a side chain include that represented by the following formula.

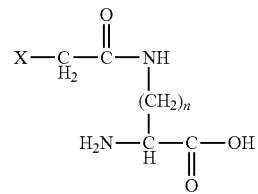

In the formula, n is an integer of 1 or more and X is a halogen atom.
n is preferably an integer satisfying 1≤n≤4, and X is preferably a chlorine atom or a bromine atom and more preferably a chlorine atom.
The amino acid represented by the above formula,
in a case where n=1, $N^3$-haloacetyl-L-2,3-diaminopropanoic acid[(2S)-2-amino-3-[(2-haloacetyl)amino]propanoic acid] or $N^3$-haloacetyl-D-2,3-diaminopropanoic acid[(2R)-2-amino-3-[(2-haloacetyl)amino]propanoic acid],
in a case where n=2, $N^4$-haloacetyl-L-2,4-diaminobutanoic acid[(2S)-2-amino-4-[(2-haloacetyl)amino]butanoic acid] or $N^4$-haloacetyl-D-2,4-diaminobutanoic acid[(2R)-2-amino-4-[(2-haloacetyl)amino]butanoic acid,
in a case where n=3, N-δ-haloacetyl-L-ornithine[(2S)-2-amino-5-[(2-haloacetyl)amino]pentanoic acid] or N-δ-haloacetyl-D-ornithine[(2R)-2-amino-5-[(2-haloacetyl)amino]pentanoic acid], and
in a case where n=4, N-ε-haloacetyl-L-lysine[(2S)-2-amino-6-[(2-haloacetyl)amino]hexanoic acid] or N-ε-haloacetyl-D-lysine[(2R)-2-amino-6-[(2-haloacetyl)amino]hexanoic acid].

(1) The thioether bond is preferably a thioether bond formed between a side chain thiol group of a first amino acid residue derived from an amino acid having a thiol group in a side chain and a side chain haloacetyl group of a second amino acid residue derived from an amino acid having a haloacetyl group in a side chain.

(2a) The thioether bond is more preferably a thioether bond formed between a side chain thiol group of a first amino acid residue derived from amino acid having a thiol group in a side chain other than L-cysteine and D-cysteine and a side chain haloacetyl group of a second amino acid residue derived from amino acid having a haloacetyl group in a side chain.

(2b) The thioether bond is more preferably a thioether bond formed between a side chain thiol group of a first amino acid residue derived from an amino acid having a thiol group in a side chain selected from the group consisting of cysteine, homocysteine, and penicillamine and a side chain haloacetyl group of a second amino acid residue derived from amino acid having a haloacetyl group in a side chain.

Examples of such a thioether bond include that represented by the following formula.

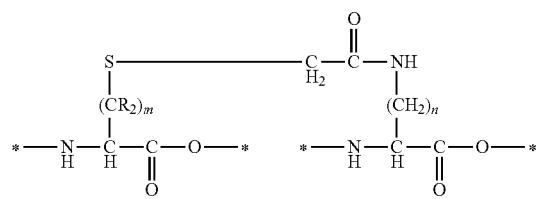

In the formula:
m is 1 or 2;
n is an integer of 1 or more;
in a case where m=1, R is a hydrogen atom or a methyl group;
in a case where m=2, R is a hydrogen atom; and
represents a coupling point with other amino acid residues or a terminal group.

In addition, n is preferably an integer satisfying 1≤n≤4.

(3) The thioether bond is further preferably a thioether bond formed between a side chain thiol group of a first amino acid residue derived from an amino acid having a thiol group in a side chain selected from the group consisting of homocysteine and penicillamine and a side chain haloacetyl group of a second amino acid residue derived from an amino acid having a haloacetyl group in a side chain.

Examples of such a thioether bond include that represented by the following formula.

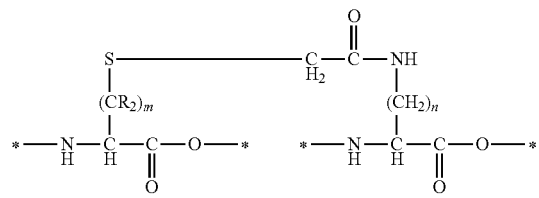

In the formula:
m is 1 or 2;
n is an integer of 1 or more;
in a case where m=1, R is a methyl group;
in a case where m=2, R is a hydrogen atom; and
represents a coupling point with other amino acid residues or other groups.

In addition, n is preferably an integer satisfying 1≤n≤4.

(4) The thioether bond is even more preferably a thioether bond formed between a side chain thiol group of a first amino acid residue derived from homocysteine and a side chain haloacetyl group of a second amino acid residue derived from amino acid having a haloacetyl group in a side chain.

Examples of such a thioether bond include that represented by the following formula.

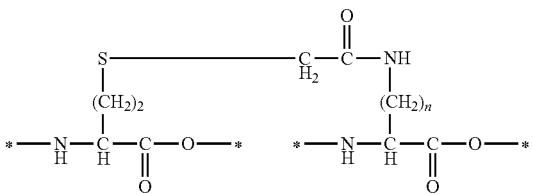

In the formula, n is an integer of 1 or more, and * represents a coupling point with other amino acid residues or other substituents. In addition, n is preferably an integer satisfying 1≤n≤4.

(Particularly Preferable Thioether Bond)

Since the thioether bond has high alkali resistance, the mixed mode affinity chromatography carrier maintains antibody binding properties even if washing is repetitively performed by alkali, and thus it is possible to decrease the antibody purification cost. Such a thioether bond is particularly preferably a thioether bond formed between a homocysteine residue and a N-ε-chloroacetyl lysine residue.

<<Triazole Bond>>

The triazole bond is not particularly limited, but preferably a triazole bond formed between a side chain azide group of a first amino acid residue derived from an amino acid having an azide group in a side chain and a side chain alkynyl group of a second amino acid residue derived from an amino acid having an alkynyl group in a side chain.

Examples of the triazole bond formed between a side chain azide group of a first amino acid residue derived from an amino acid having an azide group in a side chain and a side chain alkynyl group of a second amino acid residue derived from an amino acid having an alkynyl group in a side chain include that represented by the following formula.

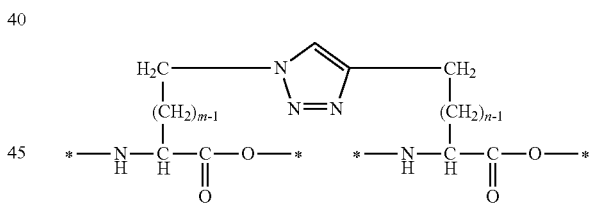

Here, * is a coupling point with other amino acid residues or other substituents, m and n are each independently an integer of 1 or more and more preferably each independently an integer of 1 or more and at least one is an integer of 2 or more.

In a case where m=1, the amino acid residue derived from an amino acid having an azide group in a side chain is an amino acid residue derived from β-azide-L-alanine or βf-azide-D-alanine, and preferably an amino acid residue derived from β-azide-L-alanine.

In a case where m=2, the amino acid residue derived from an amino acid having an azide group in a side chain is an amino acid residue derived from γ-azide-L-homoalanine or γ-azide-D-homoalanine, and preferably γ-azide-L-homoalanine.

In a case where m=3, the amino acid residue derived from an amino acid having an azide group in a side chain is an amino acid residue derived from δ-azide-L-ornithine or δ-azide-D-ornithine, and preferably δ-azide-L-ornithine.

In a case where m=4, the amino acid residue derived from an amino acid having an azide group in a side chain is an amino acid residue derived from ε-azide-L-lysine or ε-azide-D-lysine, and preferably ε-azide-L-lysine.

In a case where n=1, the amino acid residue derived from an amino acid having an alkynyl group in a side chain is an amino acid residue derived from 2-propargyl-L-glycine [(2S)-2-amino-4-pentynoic acid] or D-propargylglycine [(2R)-2-amino-4-pentynoic acid], and preferably an amino acid residue derived from 2-propargyl-L-glycine[(2S)-2-amino-4-pentynoic acid].

In a case where n=2, the amino acid residue derived from an amino acid having an alkynyl group in a side chain is 2-propargyl-L-alanine(L-homopropargylglycine)[(2S)-2-amino-5-hexynoic acid] or 2-propargyl-D-alanine(D-homopropargylglycine)[(2R)-2-amino-5-hexynoic acid], and preferably an amino acid residue derived from 2-propargyl-L-alanine(L-homopropargylglycine)[(2S)-2-amino-5-hexynoic acid].

In a case where n=3, the amino acid residue derived from an amino acid having an alkynyl group in a side chain is an amino acid residue derived from 2-propargyl-L-homoalanine(2-propargyl-L-bishomoglycine)[(2S)-2-amino-6-heptynoic acid] or 2-propargyl-D-homoalanine(2-propargyl-D-bishomoglycine)[(2R)-2-amino-6-heptynoic acid], and preferably an amino acid residue derived from 2-propargyl-L-homoalanine(2-propargyl-L-bishomoglycine)[(2S)-2-amino-6-heptynoic acid].

(Particularly Preferable Triazole Bond)

Since the triazole bond has high alkali resistance, in a case where the triazole bond is included in the intramolecular crosslinking, the mixed mode affinity chromatography carrier maintains antibody binding properties even if washing is repetitively performed by alkali, and thus it is possible to decrease the antibody purification cost. Such a triazole bond is particularly preferably a triazole bond formed between a γ-azide homoalanine residue or a ε-azide lysine residue and a homopropargylglycine residue or a bishomopropargylglycine residue.

<<Amide Bond>>

The amide bond is not particularly limited, but preferably an amide bond formed between a side chain amino group of a first amino acid residue derived from an amino acid having an amino group in a side chain and a side chain carboxy group of a second amino acid residue derived from an amino acid having a carboxy group in a side chain.

Examples of an amide bond formed between a side chain amino group of a first amino acid residue derived from an amino acid having an amino group in the side chain and a side chain carboxy group of a second amino acid residue derived from an amino acid having a carboxy group in a side chain include that represented by the following formula.

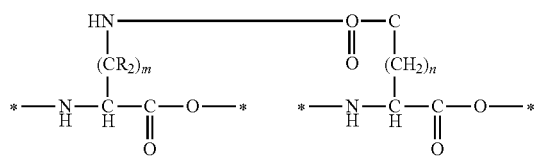

Here, * represents a coupling point with other amino acid residues or other substituents, m and n are each independently an integer of 1 or more, preferably m=1, 2, 3, or 4 and n=1, 2, or 3, and more preferably m=2 or 3 and n=1 or 2.

In a case where m=1, the amino acid residue derived from an amino acid having an amino group in a side chain is an amino acid residue derived from L-2,3-diaminopropanoic acid[(2S)-2,3-diaminopropanoic acid] or D-2,3-diaminopropanoic acid[(2R)-2,3-diaminopropanoic acid], and preferably an amino acid residue derived from L-2,3-diaminopropanoic acid[(2S)-2-aminopropanoic acid].

In a case where m=2, the amino acid residue derived from an amino acid having an amino group in a side chain is an amino acid residue derived from L-2,4-diaminobutanoic acid[(2S)-2,4-diaminobutanoic acid] or D-2,4-diaminobutanoic acid[(2R)-2,4-diaminobutanoic acid], and preferably an amino acid residue derived from L-2,4-diaminobutanoic acid[(2S)-2,4-diaminobutanoic acid].

In a case where m=3, the amino acid residue derived from an amino acid having an amino group in a side chain is an amino acid residue derived from L-ornithine[(2S)-2,5-diaminopentanoic acid] or D-ornithine[(2R)-2,5-diaminopentanoic acid], and preferably an amino acid residue derived from L-ornithine[(2S)-2,5-diaminopentanoic acid].

In a case where m=4, the amino acid residue derived from an amino acid having an amino group in a side chain is an amino acid residue derived from L-lysine[(2S)-2,6-diaminohexanoic acid] or D-lysine[(2R)-2,6-diaminohexanoic acid], and preferably an amino acid residue derived from L-lysine [(2S)-2,6-diaminohexanoic acid].

In a case where n=1, the amino acid residue derived from an amino acid having a carboxy group in a side chain is an amino acid residue derived from L-aspartic acid or D-aspartic acid, and preferably an amino acid residue derived from L-aspartic acid.

In a case where n=2, the amino acid residue derived from an amino acid having a carboxy group in a side chain is an amino acid residue derived from L-glutamic acid or D-glutamic acid, and preferably an amino acid residue derived from L-glutamic acid.

In a case where n=3, the amino acid residue derived from an amino acid having a carboxy group in a side chain is an amino acid residue derived from L-homoglutamic acid[(2S)-2-aminoadipic acid] or D-homoglutamic acid[(2R)-2-aminoadipic acid], and preferably an amino acid residue derived from L-homoglutamic acid[(2S)-2-aminoadipic acid].

(Particularly Preferable Amide Bond)

Since the amide bond has high alkali resistance, the mixed mode affinity chromatography carrier maintains antibody binding properties even if washing is repetitively performed by alkali, and thus it is possible to decrease the antibody purification cost. Such an amide bond is particularly preferably an amide bond formed between a lysine residue and a glutamic acid residue.

<<Number of Amino Acid Residues of Cyclic Portion>>

The number of amino acid residues of the cyclic portion is not particularly limited as long as the number of amino acid residues of the cyclic portion is equal to or less than the total number of amino acid residues of the cyclic peptide, but preferably 8 to 14, more preferably 9 to 13, still more preferably 10 to 12, and even more preferably 11.

<<Straight Chain Portion>>

The cyclic peptide may include a straight chain portion. The straight chain portion is a portion not included in the cyclic portion out of polypeptide chains of the cyclic peptide.

The straight chain portion may include an amino acid residue having at least one selected from the group consisting of a hydroxy group and a carboxy group in a side chain. The amino acid residue having at least one selected from the group consisting of a hydroxy group and a carboxy group in a side chain will be described later.

The straight chain portion may include an amino acid residue derived from an amino acid having an immobilized functional group in a side chain. The immobilized functional group and the amino acid having the immobilized functional group will be described later.

<<Bond of Cyclic Peptide to at Least One of Substrate or Hydrophilic Polymer>>

The cyclic peptide is preferably bonded to at least one of the substrate or the hydrophilic polymer via a covalent bond.

Examples of such a covalent bond include (a) a covalent bond between an amino acid residue side chain of the cyclic peptide straight chain portion and at least one of the substrate or the hydrophilic polymer, or (b) a covalent bond between an N-terminal or a C-terminal of the polypeptide chain of the cyclic peptide and at least one of the substrate or the hydrophilic polymer.

Examples of the covalent bond of (a) include a bond formed between an immobilized functional group of the amino acid residue side chain and a reactive functional group of at least one of the substrate or the hydrophilic polymer (functional group forming a covalent bond by reacting with the immobilized functional group). The immobilized functional group and the reactive functional group in this case will be described later.

Examples of the covalent bond of (b) include a bond via a linker between an N-terminal or a C-terminal of the polypeptide chain and a polymer main chain or a side chain of at least one of the substrate or the hydrophilic polymer, or a bond not via the linker.

Examples of the linker in this case include a polyethylene glycol (PEG) linker. The unit number of ethylene glycol of the PEG linker is not particularly limited as long as the unit number thereof is 1 or more, but preferably 1 to 24, more preferably 1 to 12, and still more preferably 4 to 8.

<<Molecular Weight of Cyclic Peptide>>

The molecular weight of the cyclic peptide is not particularly limited, but preferably equal to or less than 10,000 from a viewpoint of synthesis cost, and preferably equal to or less than 5,000 from a viewpoint of antigenicity. The molecular weight of the cyclic peptide is more preferably equal to or less than approximately 4,000, still more preferably equal to or less than approximately 3,000, and most preferably equal to or less than approximately 2,000, where "approximately" means that a range of ±2% is included.

The molecular weight of the cyclic peptide is a molecular weight combining the cyclic portion and the straight chain portion.

In a case where the molecular weight is less than 5,000, antigenicity is decreased, and antigenicity is substantially not shown.

In addition, the number of the amino acid residues of the cyclic peptide is not particularly limited, but preferably equal to or less than 100, more preferably equal to or less than 50, still more preferably equal to or less than 40, even more preferably equal to or less than 30, and even more preferably equal to or less than 20.

The number of the amino acid residues of the cyclic peptide is the number of the amino acid residues combining the cyclic portion and the straight chain portion.

<<Antibody Binding Properties>>

In the present invention, antibody binding properties means binding properties with an antibody and/or an antibody derivative.

As the antibody binding properties becomes high, in a case of being used as an affinity ligand of the affinity chromatography carrier, adsorptive force of the antibody is high and the antibody is hardly desorbed even at the time of washing.

The antibody refers to an immunoglobulin or an analog, fragment or fusion thereof.

The immunoglobulin may be any of the five classes (isotypes) of Immunoglobulin G (IgG), Immunoglobulin M (IgM), Immunoglobulin A (IgA), Immunoglobulin D (IgD), and Immunoglobulin E (IgE), but is preferably IgG or IgM, and more preferably IgG.

In addition, the analog refers to a naturally occurring or artificially constructed protein or protein conjugate in which the structure or function of the immunoglobulin is at least partially retained.

In addition, the fragment refers to a protein having a partial structure of the immunoglobulin which is constructed by enzymatic treatment or genetic engineering design.

In addition, the fusion refers to a protein constructed by fusing a functional part of the protein including biological activity of various cytokine, cytokine receptor, and the like with the entirety or a part of the immunoglobulin by genetic engineering.

In addition, the derivative refers to a chimeric antibody in which an Fc region of a human immunoglobulin and an Fab region of a non-human mammalian immunoglobulin are fused, a chimeric antibody in which several Fc regions of a human immunoglobulin and several Fv regions of a non-human mammalian immunoglobulin are fused, a non-human mammalianized antibody in which the remaining portion excluding a complementarity determining region (CDR) portion of a non-human mammalian immunoglobulin and a human immunoglobulin CDR portion are fused, a chimeric antibody in which an Fc region of a non-human mammalian immunoglobulin and a Fragment, antigen binding (Fab) region of a human immunoglobulin are fused, a chimeric antibody in which several Fc regions of a non-human mammalian immunoglobulin and several Fv regions of a human immunoglobulin are fused, a human antibody in which the remaining portion excluding a CDR portion of a human immunoglobulin and a non-human mammalian immunoglobulin CDR portion are fused, a chimeric antibody in which an Fc region of a non-human mammalian immunoglobulin and an Fab region of a non-human mammalian immunoglobulin are fused, a chimeric antibody in which several Fc regions of a non-human mammalian globulin and several Fv regions of a non-human mammalian immunoglobulin are fused, a chimeric antibody in which several Fc regions of a non-human mammalian immunoglobulin and several Fv regions of a non-human mammalian immunoglobulin are fused, a non-human mammalian antibody in which the remaining portion excluding a complementarity determining region (CDR) portion of a non-human mammalian immunoglobulin and a non-human mammalian immunoglobulin CDR portion are fused, or a chemically modified protein thereof which retains an Fc region.

The antibody is preferably a monoclonal antibody or a fusion having an Fc region of immunoglobulin, and more preferably a monoclonal antibody.

<<More Specific Description of Cyclic Peptide>>

The cyclic peptide will be more specifically described. Here, the cyclic peptide before being introduced into the mixed mode affinity chromatography carrier of the present invention as an affinity ligand will be described.

In the present invention, amino acids are, in principle, represented using names, abbreviations, and the like employed by INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Biochemical Nomenclature (JCBN). In addition, amino acid residues are represented using abbreviations of amino acids from which the amino acid residues are derived. The amino acid residues include an N-terminal amino acid (N-terminal residue) and C-terminal amino acid (C-terminal residue).

Unless otherwise specified, amino acid sequences (also referred to as "primary structure") of a peptide or a protein one-dimensionally represent such that from the left end to the right end is from the N-terminal to the C-terminal. In a case where the amino acid residue in the amino acid sequence of the peptide or the protein is specified including the position, the amino acid residue is sometimes represented by adding the number indicating the position of the amino acid residue from the N-terminal side on a right side of the abbreviation of the amino acid residue. For example, there is a case where a second L-lysine from the N-terminal is represented as Lys2.

In addition, in a case where an amino acid is represented using the name, in a case where there are isomers in the enantiomer relationship, that is, L bodies and D bodies, in principle, L bodies are represented, except the case where distinction between L bodies and D bodies are explicitly indicated. For example, "isoleucine" represents "L-isoleucine", and enantiomer of "isoleucine" represents "D-isoleucine". The same applies to the amino acid residues.

In addition, in a case where an amino acid is represented using an abbreviation thereof (three-letter abbreviation or one-letter abbreviation), in a case where there are isomers in the enantiomer relationship, that is, L bodies and D bodies, in principle, L bodies are represented, except the case where distinction between L bodies and D bodies are explicitly indicated. However, "X" representing an optional amino acid is not limited thereto. For example, both of "Lys" and "L-Lys" represent "L-lysine", and "D-Lys" represents "D-lysine". The same applies to the amino acid residues.

In addition, in a state in which an amino acid is represented using the name, in a case where there are isomers in the diastereomer relationship, the isomer is not included in the amino acid specified by the name. The diastereomer uses a prefix "allo" to treat them as different kinds of amino acids. For example, "threonine" and "L-threonine" do not include "L-allothreonine", and "D-threonine" does not include "D-allothreonine". The same applies to the amino acid residues.

The names and abbreviations of the amino acids in which 1-letter abbreviations and 3-letter abbreviations are officially recognized are shown in Table 1.

TABLE 1

| 1-Letter abbreviation | 3-Letter abbreviation | Name |
|---|---|---|
| A | Ala | L-Alanine |
| B | Asx | L-Aspartic acid or L-Asparagine |
| C | Cys | L-Cysteine |
| D | Asp | L-Aspartic acid |
| E | Glu | L-Glutamic acid |
| F | Phe | L-Phenylalanine |
| G | Gly | Glycine |
| H | His | L-Histidine |
| I | Ile | L-Isoleucine |
| K | Lys | L-Lysine |
| L | Leu | L-Leucine |
| M | Met | L-Methionine |
| N | Asn | L-Asparagine |

TABLE 1-continued

| 1-Letter abbreviation | 3-Letter abbreviation | Name |
|---|---|---|
| O | Pyl | L-Pyrrolysine |
| P | Pro | L-Proline |
| Q | Gln | L-Glutamine |
| R | Arg | L-Arginine |
| S | Ser | L-Serine |
| T | Thr | L-Threonine |
| U | Sec | L-Selenocysteine |
| V | Val | L-Valine |
| W | Trp | L-Tryptophan |
| X | Xaa | Optional amino acid |
| Y | Tyr | L-Tyrosine |
| Z | Glx | L-Glutamic acid or L-Glutamine |

The amino acids are not limited to those exemplified in Table 1, and amino acids named unusual amino acids can be used. Examples of the unusual amino acids are exemplified in the following Table 2, but are not limited thereto.

TABLE 2

| 3-Letter abbreviation | Name |
|---|---|
| Aad | Homoglutamic acid |
| βAad | 3-Aminoadipic acid |
| Abu | 2-Aminobutanic acid |
| A$_2$bu | 2,4-Diaminobutanic acid |
| Ahx | 2-Aminohexanoic acid |
| Ahe | 2-Aminoheptanoic acid |
| Aib | 2-Aminoisobutyric acid |
| εAhx | 6-Aminohexanoic acid |
| βAla | β-Alanine |
| Ape | 2-Aminopentanoic acid |
| A$_2$pr | 2,3-Diaminopropanoic acid |
| Apm | 2-Aminopimelic acid |
| A$_2$pm | 2,6-Diaminopimelic acid |
| Cit | Citrulline |
| Cya | Cysteic acid |
| Dbu | 2,4-Diaminobutanoic acid |
| Dpm | 2,6-Diaminopimelic acid |
| Dpr | 2,3-Diaminopropanoic acid |
| Gla | 4-Carboxyglutamic acid |
| Glp | 5-Oxoproline |
| Hcy | Homocysteine |
| Hse | Homoserine |
| Hsl | Homoserinelactone |
| 5Hyl | 5-Hydroxylysine (Hyl) |
| aHyl | Allohydroxylysine |
| 3Hyp | 3-Hydroxyproline |
| 4Hyp | 4-Hydroxyproline |
| aIle | Alloisoleucine |
| Nle | Norleucine |
| Nva | Norvaline |
| Orn | Ornithine |
| Sar | Sarcosine |
| aThr | Allothreonine |
| Thx | Thyroxine |
| Pen | Penicillamine |

<<Formula (I)>>

The cyclic peptide is preferably a cyclic peptide represented by the following formula (I).

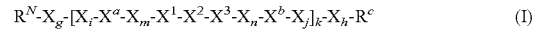

$$R^N\text{-}X_g\text{-}[X_i\text{-}X^a\text{-}X_m\text{-}X^1\text{-}X^2\text{-}X^3\text{-}X_n\text{-}X^b\text{-}X_j]_k\text{-}X_h\text{-}R^c \quad (I)$$

In the formula (I), for example, $X_n$ means that n Xs are linked. In other words, $X_n$ is also referred to as $-(X)_n-$. The definition of $X_g$, $X_i$, $X_m$, $X_j$, and $X_h$ are also the same as that of the $X_n$.

(Cyclic Portion, Straight Chain Portion, Crosslinking Portion, and Antibody Binding Portion)

In the cyclic peptide used in the mixed mode affinity chromatography carrier of the present invention, out of a polypeptide chain, a portion of a ring closed by crosslinking is referred to as a cyclic portion, and a portion not included in the cyclic portion is referred to as a straight chain portion. In addition, out of the cyclic portion, a portion forming an intramolecular crosslinked structure of the cyclic peptide of the present invention is referred to as a crosslinking portion, and a portion strongly contributing to antibody binding properties of the cyclic peptide of the present invention is referred to as an antibody binding portion.

The cyclic portion of the cyclic peptide represented by the formula (I) is a "$X^a$-$X_m$-$X^1$-$X^2$-$X^3$-$X_n$-$X^b$" portion, the straight chain portion is "$X_g$", "$X_h$", "$X_i$", and "$X_j$", the crosslinking portion is "$X^a$" and "$X^b$", and the antibody binding portion is "$X^1$-$X^2$-$X^3$".

In addition, in the formula (1), there is a case where [$X_i$-$X^a$-$X_m$-$X^1$-$X^2$-$X^3$-$X_n$-$X^b$-$X_j$] is referred to as a repeating portion.

($X^1$, $X^2$, and $X^3$)

In the formula (1), $X^1$ is an L-leucine residue, an L-isoleucine residue, an L-methionine residue, an L-lysine residue, or an L-arginine residue, preferably an L-leucine residue or an L-isoleucine residue, and more preferably an L-leucine residue.

In addition, in the formula (1), $X^2$ is an L-valine residue or an L-isoleucine residue, and preferably an L-valine residue.

In addition, in the formula (1), $X^3$ is an L-tryptophan residue or an L-phenylalanine residue, and preferably an L-tryptophan residue.

($X^a$ and $X^b$)

In the formula (I), $X^a$ and $X^b$ are any of one of the following (a) to (d).

(a) $X^a$ and $X^b$ are crosslinked by a disulfide bond.

$X^a$ and $X^b$ are preferably each independently an amino acid residue derived from an amino acid having a thiol group in a side chain, more preferably, at least one of $X^a$ or $X^b$ is an amino acid residue derived from an amino acid having a thiol group in a side chain other than L-cysteine and D-cysteine, and still more preferably, both of $X^a$ and $X^b$ are an amino acid residue derived from an amino acid having a thiol group in a side chain other than L-cysteine and D-cysteine.

That is, the disulfide bond between $X^a$ and $X^b$ is preferably a disulfide bond between two amino acid residues derived from an amino acid having a thiol group in a side chain, more preferably a disulfide bond between an amino acid residue derived from an amino acid having a thiol group in a side chain other than L-cysteine and D-cysteine and an amino acid residue derived from an amino acid having a thiol group in a side chain, and still more preferably a disulfide bond between two amino acid residues including a thiol group in a side chain other than L-cysteine and D-cysteine.

Drug resistance of the cyclic peptide crosslinked by the disulfide bond between $X^a$ and $X^b$ is generally higher in a case where one of $X^a$ and $X^b$ is an amino acid residue derived from an amino acid having a thiol group in a side chain other than L-cysteine and D-cysteine compared to a case where both of $X^a$ and $X^b$ are an amino acid residue derived from L-cysteine and D-cysteine, and further higher in a case where both of $X^a$ and $X^b$ are an amino acid residue derived from an amino acid having a thiol group in a side chain other than L-cysteine and D-cysteine. That is, from a viewpoint of drug resistance, the disulfide bond is more preferably a disulfide bond other than the disulfide bond between two amino acid residues derived from L-cysteine and D-cysteine, still more preferably a disulfide bond between two amino acid residues derived from an amino acid having a thiol group in a side chain other than L-cysteine and D-cysteine, and particularly preferably a disulfide bond between two amino acid residues derived from homocysteine.

Examples of the amino acid having a thiol group in a side chain include L-cysteine, D-cysteine, L-homocysteine, D-homocysteine, L-penicillamine, and D-penicillamine, and the amino acid is preferably an amino acid selected from the group consisting of cysteine, homocysteine, and penicillamine.

In addition, examples of the amino acid having a thiol group in a side chain other than L-cysteine and D-cysteine include L-homocysteine, D-homocysteine, L-penicillamine, and D-penicillamine, and the amino acid is preferably an amino acid selected from the group consisting of homocysteine and penicillamine.

(b) $X^a$ and $X^b$ are crosslinked by a thioether bond.

Among $X^a$ and $X^b$, preferably, one is an amino acid residue derived from an amino acid having a thiol group in a side chain and the other is an amino acid residue derived from an amino acid having a haloacetyl group in a side chain.

The amino acid having a thiol group in a side chain is preferably an amino acid having a thiol group in a side chain other than L-cysteine and D-cysteine.

In addition, the amino acid having a thiol group in a side chain is preferably an amino acid having a thiol group in a side chain selected from the group consisting of cysteine, homocysteine, and penicillamine.

In addition, the amino acid having a thiol group in a side chain is more preferably an amino acid having a thiol group in a side chain selected from the group consisting of homocysteine and penicillamine, and still more preferably homocysteine.

The amino acid having a haloacetyl group in a side chain is preferably an amino acid represented by the following formula.

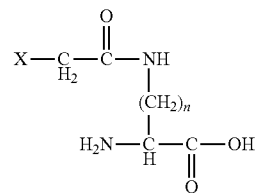

In the formula, n is an integer of 1 or more, and X is a halogen atom.

n is preferably an integer satisfying 1≤n≤4, and X is preferably a chlorine atom or a bromine atom and more preferably a chlorine atom.

In a case where n=1, the formula represents N'-haloacetyl-L-2,3-diaminopropanoic acid[(2S)-2-amino-3-[(2-haloacetyl)amino]propanoic acid] or $N^3$-haloacetyl-D-2,3-diaminopropanoic acid[(2R)-2-amino-3-[(2-haloacetyl)amino]propanoic acid], in a case where n=2, the formula represents $N^4$-haloacetyl-L-2,4-diaminobutanoic acid[(2S)-2-amino-4-[(2-haloacetyl)amino]butanoic acid] or $N^4$-haloacetyl-D-2,4-diaminobutanoic acid[(2R)-2-amino-4-[(2-haloacetyl)amino]butanoic acid], in a case where n=3, the formula represents N-δ-haloacetyl-L-ornithine[(2S)-2-amino-5-[(2-haloacetyl)

amino]pentanoic acid] or N-δ-haloacetyl-D-ornithine [(2R)-2-amino-5-[(2-haloacetyl)amino]pentanoic acid], and in a case where n=4, the formula represents N-ε-haloacetyl-L-lysine[(2S)-2-amino-6-[(2-haloacetyl)amino]hexanoic acid] or N-ε-haloacetyl-D-lysine[(2R)-2-amino-6-[(2-haloacetyl)amino]hexanoic acid].

The amino acid having a haloacetyl group in a side chain is particularly preferably N-ε-chloroacetyl-L-lysine, N-ε-chloroacetyl-D-lysine, N-δ-chloroacetyl-L-ornithine, or N-δ-chloroacetyl-D-ornithine, more particularly preferably N-ε-chloroacetyl-L-lysine or N-δ-chloroacetyl-L-ornithine, and most preferably N-δ-chloroacetyl-L-ornithine.

(c) $X^a$ and $X^b$ are crosslinked by a triazole bond.

Among $X^a$ and $X^b$, preferably, one is an amino acid residue derived from an amino acid having an azide group in a side chain and the other is an amino acid residue derived from an amino acid having an alkynyl group in a side chain.

Here, the triazole bond is a bond in which an azide group and an alkynyl group are formed by Huisgen reaction represented by the following formula.

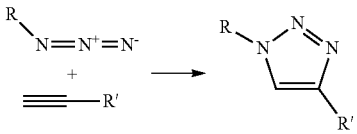

In the formula. R represents a portion other than an azide group of an amino acid residue having an azide group in a side chain, and $R^1$ represents a portion other than an ethynyl group of an amino acid residue having an alkynyl group in a side chain.

Examples of the amino acid having an azide group in a side chain include that represented by the following formula, where m is an integer of 1 or more.

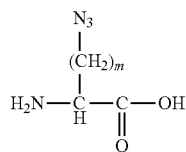

m is not particularly limited as long as m is equal to or more than 1, but from a viewpoint of economic efficiency, m is preferably 1≤m≤4, more preferably 2≤m≤4, still more preferably 3≤m≤4, and even more preferably 4.

In a case where m=1, the amino acid having an azide group in a side chain represented by the formula is β-azide-L-alanine or β-azide-D-alanine, and preferably δ-azide-L-alanine.

In a case where m=2, the amino acid having an azide group in a side chain represented by the formula is γ-azide-L-homoalanine or γ-azide-D-homoalanine, and preferably γ-azide-L-homoalanine.

In a case where m=3, the amino acid having an azide group in a side chain represented by the formula is δ-azide-L-ornithine or 5-azide-D-ornithine, and preferably δ-azide-L-ornithine.

In a case where m=4, the amino acid having an azide group in a side chain represented by the formula is ε-azide-L-lysine or ε-azide-D-lysine, and preferably ε-azide-L-lysine.

The amino acid having an azide group in a side chain is particularly preferably ε-azide-L-lysine, S-azide-L-ornithine, or γ-azide-L-homoalanine, more particularly preferably ε-azide-L-lysine or δ-azide-L-ornithine, and most preferably ε-azide-L-lysine.

Examples of the amino acid having an alkynyl group in a side chain include that represented by the following formula, where n is an integer of 1 or more.

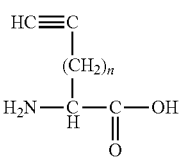

n is not particularly limited as long as n is equal to or more than 1, but from a viewpoint of economic efficiency, is preferably 1≤n≤3, and more preferably 2≤n≤3.

In a case where n=1, the amino acid having an alkynyl group in a side chain represented by the formula is 2-propargyl-L-glycine or 2-propargyl-D-glycine, and preferably 2-propargyl-L-glycine.

In a case where n=2, the amino acid having an alkynyl group in a side chain represented by the formula is 2-propargyl-L-alanine (2-propargyl-L-homoglycine) or 2-propargyl-D-alanine (2-propargyl-D-homoglycine), and preferably 2-propargyl-L-alanine (2-propargyl-L-homoglycine).

In a case where n=3, the amino acid having an alkynyl group in a side chain represented by the formula is 2-propargyl-L-homoalanine (2-propargyl-L-bishomoglycine) or 2-propargyl-D-homoalanine (2-propargyl-D-bishomoglycine), and preferably 2-propargyl-L-homoalanine (2-propargyl-L-bishomoglycine).

The amino acid having an alkynyl group in a side chain is particularly preferably 2-propargyl-L-alanine (2-propargyl-L-homoglycine) or 2-propargyl-L-homoalanine (2-propargyl-L-bishomoglycine), and more particularly preferably 2-propargyl-L-homoalanine (2-propargyl-L-bishomoglycine).

(d) $X^a$ and $X^b$ are crosslinked by an amide bond.

Among $X^a$ and $X^b$, one is preferably an amino acid residue derived from an amino acid having an amino group in a side chain and the other is an amino acid residue derived from an amino acid having a carboxy group in a side chain.

Examples of the amino acid having an amino group in a side chain include that represented by the following formula, where m is an integer of 1 or more.

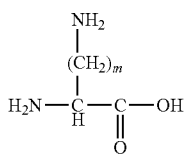

m is not particularly limited as long as m is 1 or more, but from a viewpoint of economic efficiency, m is preferably 1≤m≤4, more preferably 2≤m≤4, still more preferably 3≤m≤4, and even more preferably m=4.

In a case where m=1, an amino acid having an amino group in a side chain represented by the formula is L-2,3-diaminopropanoic acid[(2S)-2,3-diaminopropanoic acid] or D-2,3-diaminopropanoic acid[(2R)-2,3-diaminopropanoic acid], and preferably L-2,3-diaminopropanoic acid[(2S)-2,3-diaminopropanoic acid].

In a case where m=2, an amino acid having an amino group in a side chain represented by the formula is L-2,4-diaminobutanoic acid[(2S)-2,4-diaminobutanoic acid] or D-2,4-diaminobutanoic acid[(2R)-2,4-diaminobutanoic acid], and preferably L-2,4-diaminobutanoic acid[(2S)-2,4-diaminobutanoic acid].

In a case where m=3, an amino acid having an amino group in a side chain represented by the formula is L-ornithine or D-ornithine, and preferably L-ornithine.

In a case where m=4, an amino acid having an amino group in a side chain represented by the formula is L-lysine or D-lysine, and preferably L-lysine.

Examples of the amino acid having a carboxy group in a side chain include that represented by the following formula, where n is an integer of 1 or more.

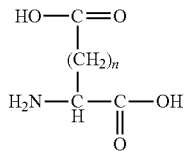

n is not particularly limited as long as n is 1 or more, but from a viewpoint of economic efficiency, n is preferably $1 \le n \le 3$, more preferably n=1 or 2, and still more preferably n=2.

In a case where n=1, an amino acid having a carboxy group in a side chain represented by the formula is L-aspartic acid or D-aspartic acid, and preferably L-aspartic acid.

In a case where n=2, an amino acid having a carboxy group in a side chain represented by the formula is L-glutamic acid or D-glutamic acid, and preferably L-glutamic acid.

In a case where n=3, an amino acid having a carboxy group in a side chain represented by the formula is L-homoglutamic acid or D-homoglutamic acid, and preferably L-homoglutamic acid.

(X)

In the formula (I), X represents an amino acid residue, and in a case where X is in multiple numbers, a plurality of X may be the same or different.

X is not particularly limited as long as X is an amino acid residue, preferably an amino acid residue derived from an amino acid selected from the group consisting of amino acids shown in Table 1 (excluding B, Z, and X) and amino acids shown in Table 2, and more preferably an amino acid residue derived from an amino acid selected from the group consisting of amino acids shown in Table 1 (excluding B, Z, and X). In addition, in a case of existence, X may be an amino acid residue derived from an enantiomer or a diastereomer of such amino acids.

(N-Terminal Group and C-Terminal Group)

In the formula (I), $R^N$ represents an N-terminal group.

Examples of the N-terminal group include an amino group, and the amino group may be subjected to N-terminal modification such as N-acetylation, N-formylation, or N-acylation.

In the formula (I), $R^C$ represents a C-terminal group.

Examples of the C-terminal group include a carboxy group, and the carboxy group may be subjected to C-terminal modification such as amidation.

(g and h)

In the formula (I), g and h each independently are an integer of 0 or more, g preferably satisfies $0 \le g \le 20$, more preferably satisfies $0 \le g \le 10$, and still more preferably satisfies $0 \le g \le 5$.

h preferably satisfies $0 \le h \le 20$, more preferably satisfies $0 \le h \le 10$, and still more preferably satisfies $0 \le h \le 5$.

(i and j)

In the formula (I), i and j each independently are an integer of 0 or more.

i preferably satisfies $0 \le i \le 20$, more preferably satisfies $0 \le i \le 10$, and still more preferably satisfies $0 \le i \le 5$.

j preferably satisfies $0 \le j \le 20$, more preferably satisfies $0 \le j \le 10$, and still more preferably satisfies $0 \le j \le 5$.

(m and n)

In the formula (I), m and n are integers that satisfy $0 \le m \le 9$ and $0 \le n \le 9$, respectively.

In addition, m and n satisfy $3 \le m+n \le 9$, preferably satisfy $4 \le m+n \le 8$, and still more preferably satisfy $5 \le m+n \le 7$.

(Number of Amino Acid Residues of Cyclic Portion)

In the formula (I), the number of amino acid residues [(m+n+5) residues] of a cyclic portion $[X^a\text{-}X_m\text{-}X^1\text{-}X^2\text{-}X^3\text{-}X_n\text{-}X^b]$ is 8 to 14, preferably 9 to 13, and still more preferably 10 to 12.

In a case where the number of the amino acid residues of a cyclic portion is within the range, the intramolecular strain of the cyclic peptide does not become too large and the higher-order structure such as a helix is stabilized. Therefore, the antibody binding properties of the cyclic peptide of the present invention is excellent.

(k)

k is an integer that satisfies $k \ge 1$, preferably $1 \le k \le 3$, more preferably $1 \le k \le 2$, and still more preferably k=1.

The number of repeating units are not particularly limited, but the greater the number of the repeating units, the more cyclic portions can be included. Therefore, there is a possibility that antibody binding properties of the cyclic peptide is improved. Meanwhile, the smaller the number of the repeating units, the smaller the total number of the amino acid residues. Therefore, there is a possibility that antigenicity of the cyclic peptide is suppressed. From a viewpoint of synthesis cost of the cyclic peptide, the number of the amino acid residues is preferably small, and the number of the repeating units is preferably small.

(Difference Between Repeating Units in Case where $k \ge 2$)

In addition, in a case where $k \ge 2$, that is, in a case where the cyclic peptide represented by the formula (I) contains two or more of repeating units $[X_i\text{-}X^a\text{-}X_m\text{-}X^1\text{-}X^2\text{-}X^3\text{-}X_n\text{-}X^b\text{-}X_j]$, $X^1$, $X^2$, $X^3$, $X^a$, $X^b$, $X_i$, $X_j$, $X_m$, and $X_n$ in the repeating units each may be the same, or different between the repeating units.

(Total Number of Amino Acid Residues of Cyclic Peptide)

In addition, in the formula (I), the total number of the amino acid residues of the cyclic peptide is preferably 8 to 50, more preferably 9 to 40, still more preferably 10 to 30, and even more preferably 10 to 20.

That is, in the formula (I), g, h, j, j, m, n, and k preferably satisfy $8 \le g+h+(i+j+m+n+5) \times k \le 50$, more preferably satisfy $9 \le g+h+(i+j+m+n+5) \times k \le 40$, still more preferably satisfy $10 \le g+h+(i+j+m+n+5) \times k \le 30$, and even more preferably satisfy $10 \le g+h+(i+j+m+n+5) \times k \le 20$.

In general, the greater the number of the amino acid residues, the higher the synthesis cost. Therefore, from a viewpoint of economic efficiency, the total number of the amino acid residues is preferably small.

<<Formula (IA)>>

In addition, the cyclic peptide is more preferably a cyclic peptide represented by the following formula (IA).

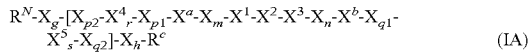

(IA)

In the formula (IA), any of $R^N$, $R^C$, $X^1$, $X^2$, $X^3$, $X^a$, $X^b$, $X_g$, $X_h$, $X_m$, $X_n$, X, g, h, m, n, and k is the same as those in the formula (I).

In addition, in the formula (IA), similar to $X_n$ in the formula (I), $X_n$ means that n Xs are linked. The same applies to $X_m$, $X_{p1}$, $X_{p2}$, $X_{q1}$, and $X_{q2}$.

In addition, in the formula (IA), $X^4_r$ and $X^5_s$ mean that r $X^4$s are linked, and s $X^5$s are linked, respectively.

(Cyclic Portion, Straight Chain Portion, Crosslinking Portion, and Antibody Binding Portion)

Straight chain portions of the cyclic peptide represented by the formula (IA) are "$X_g$", "$X_h$", "$X_{p2}$-$X^4_r$-$X_{p1}$", and "$X_{q1}$-$X^5_s$-$X_{q2}$". A cyclic portion, a crosslinking portion, and an antibody binding portion are the same as the cyclic peptide represented by the formula (I).

In addition, in the formula (IA), the repeating unit is $[X_{p2}-X^4_r-X_{p1}-X^a-X_m-X^1-X^2-X^3-X_n-X^b-X_q X^5_s-X_{q2}]$.

($X^4$ and $X^5$)

In the formula (IA), $X^4$ and $X^5$ each independently represent an amino acid residue derived from an amino acid having a carboxy group in a side chain or an amino acid residue derived from an amino acid having a hydroxy group in a side chain.

Examples of the amino acid having a carboxy group in a side chain include L-aspartic acid. D-aspartic acid. L-glutamic acid, D-glutamic acid. L-homoglutamic acid, and D-homoglutamic acid.

Examples of the amino acid having a hydroxy group in a side chain include L-serine, D-serine, L-homoserine, D-homoserine, L-tyrosine, D-tyrosine, L-threonine, D-threonine, L-allothreonine, and D-allothreonine.

The $X^4$ and $X^5$ are preferably each independently an amino acid residue selected from the group consisting of L-serine residue, D-serine residue, L-homoserine residue, D-homoserine residue, L-aspartic acid residue, D-aspartic acid residue, L-glutamic acid residue, D-glutamic acid residue, L-homoglutamic acid residue, D-homoglutamic acid residue, L-tyrosine residue, D-tyrosine residue, L-homotyrosine residue, D-homotyrosine residue, L-threonine residue, D-threonine residue, L-allothreonine residue, and D-allothreonine, more preferably each independently an amino acid residue selected from the group consisting of L-aspartic acid residue, D-aspartic acid residue, L-threonine residue, and D-threonine residue, and still more preferably $X^4$ is L-aspartic acid residue and $X^5$ is L-threonine residue.

In a case where the $X^4$ and $X^5$ are each independently an amino acid residue derived from an amino acid having a carboxy group in a side chain or an amino acid residue derived from an amino acid having a hydroxy group in a side chain, it is considered that the antibody binding portion of the cyclic portion and the antibody can further strongly interact by hydrogen bond and/or electrostatic interaction, and antibody binding properties are improved.

(p1, p2, q1, and q2)

In the formula (I), p1, p2, q1, and q2 are each independently an integer of 0 or more.

p1 preferably satisfies 0≤p1≤20, more preferably satisfies 0≤p1≤10, still more preferably satisfies 0≤p1≤5, and even more preferably 0≤p1≤2.

p2 preferably satisfies 0≤p2≤20, more preferably satisfies 0≤p2≤10, still more preferably satisfies 0≤p2≤5, and even more preferably 0≤p2≤2.

q1 preferably satisfies 0≤q1≤20, more preferably satisfies 0≤q1≤10, still more preferably satisfies 0≤q1≤5, and even more preferably 0≤q1≤2.

q2 preferably satisfies 0≤q2≤20, more preferably satisfies 0≤q2≤10, still more preferably satisfies 0≤q2≤5, and even more preferably 0≤q2≤2.

(r and s)

In the formula (IA), r and s each are an integer that satisfies 0≤r≤5, 0≤s≤5, and 1≤Max (r, s)≤5, preferably an integer that satisfies 0≤r≤4, 0≤s≤4, and 1≤Max (r, s)≤4, and more preferably an integer that satisfies 0≤r≤3, 0≤s≤3, and 1≤Max (r, s)≤3.

In a case where r≠s, Max(r, s) represents the greater one out of two numbers of r and s, and in a case where r=s, Max(r, s) represents r or s.

(Number of Amino Acid Residues of Cyclic Portion)

In the formula (IA), the number of amino acid residues [(m+n+5) residues] of the cyclic portion $[X^a-X_m-X^1-X^2-X^3-X_n-X^b]$ is 8 to 14, preferably 9 to 13, and more preferably 10 to 12, similar to the formula (I).

In a case where the number of the amino acid residues of the cyclic portion is within the range, the intramolecular strain of the cyclic peptide does not become too large and the higher-order structure such as a helix is stabilized. Therefore, the antibody binding properties of the cyclic peptide of the present invention is excellent.

(Difference Between Repeating Units in Case where k≥2)

In addition, in a case where k?2, that is, in a case where the cyclic peptide represented by the formula (IA) contains two or more of repeating units $[X_{p2}-X^4_r-X_{p1}-X^a-X_m-X^1-X^2-X^3-X_n-X^b-X_{q1}-X^5_s-X_{q2}]$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in the repeating units each may be the same, or different between the repeating units.

(Total Number of Amino Acid Residues of Cyclic Peptide)

In addition, in the formula (IA), the total number of the amino acid residues of the cyclic peptide is preferably 8 to 50, more preferably 9 to 40, still more preferably 10 to 30, and even more preferably 10 to 20.

That is, in the formula (IA), g, h, j, j, m, n, p1, p2, q1, q2, r, s, and k preferably satisfy 8≤g+h+(m+n+p1+p2+q1+q2+r+s+5)×k≤50, more preferably satisfy 9≤g+h+(m+n+p1+p2+q1+q2+r+s+5)×k≤40, still more preferably satisfy 10≤g+h+(m+n+p1+p2+q1+q2+r+s+5)×k≤30, and even more preferably satisfy 10≤g+h+(m+n+p1+p2+q1+q2+r+s+5)×k≤20.

In general, the greater the number of the amino acid residues, the higher the synthesis cost. Therefore, from a viewpoint of economic efficiency, the total number of the amino acid residues is preferably small.

<<Formula (IB)>>

In addition, the cyclic peptide is more preferably cyclic peptide represented by the following formula (IB).

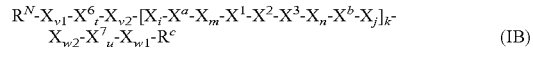

(IB)

In the formula (IB), any of $R^N$, $R^C$, $X^1$, $X^2$, $X^3$, $X^a$, $X^b$, $X_i$, $X_j$, $X_m$, $X_n$, X, i, j, m, n, and k is the same as those in the formula (I).

In addition, in the formula (IB), similar to $X_n$ in the formula (I), $X_n$ means that n Xs are linked. The same applies to $X_m$, $X_{v1}$, $X_{v2}$, $X_{w1}$, and $X_{w2}$.

In addition, in the formula (IB), $X^6_t$ and $X^7_u$ mean that t $X^6$s are linked, and u $X^7$s are linked, respectively.

(Cyclic Portion, Straight Chain Portion, Crosslinking Portion, and Antibody Binding Portion)

The straight chain portion of the cyclic peptide represented by the formula (IB) is "$X_i$", "$X_j$", "$X_{v1}$-$X^6_t$-$X_{v2}$", and "$X_{w2}$-$X^7_u$-$X_{w1}$". The cyclic portion, the crosslinking portion, and the antibody binding portion are the same as those of the cyclic peptide represented by the formula (I).

In addition, in the formula (IB), similar to the formula (I), the repeating unit is $[X_i\text{-}X^a\text{-}X_m\text{-}X^1\text{-}X^2\text{-}X^3\text{-}X_n\text{-}X^b\text{-}X_j]$.

($X^6$ and $X^7$)

In the formula (IB), $X^6$ and $X^7$ each independently represent an amino acid residue derived from an amino acid having an immobilized functional group in a side chain, and in a case where $X^6$ or $X^7$ is in multiple numbers, a plurality of $X^6$ and $X^7$ may be the same or different.

The "immobilized functional group" refers to a functional group that can form a covalent bond by reacting with a functional group (sometimes referred to as a "reactive functional group") on a substrate and/or a hydrophilic polymer.

Examples of such an immobilized functional group include an amino group, a carboxy group, a hydroxy group, a thiol group, a formyl group (aldehyde group), a carbamoyl group, an azide group, and an alkynyl group.

Examples of combination of the immobilized functional group included in the cyclic peptide and the functional group on a substrate and/or a hydrophilic polymer include an amino group and a carboxy group (amide bond forming reaction), an amino group and a formyl group (reductive amination reaction), an amino group and an epoxy group, a carboxy group and a hydroxy group (ester bond forming reaction), a thiol group and a thiol group (disulfide bond), a thiol group and an epoxy group, and an azide group and an alkynyl group (Huisgen cycloaddition reaction).

By forming a covalent bond by reacting the immobilized functional group included in the cyclic peptide with the functional group on a substrate and/or a hydrophilic polymer, the cyclic peptide is immobilized to a carrier. A covalent bond may be formed by reacting at least a part of the immobilized functional group included in the cyclic peptide with the functional group on a substrate and/or a hydrophilic polymer, and all of the immobilized functional groups may not react with the functional group on a substrate and/or a hydrophilic polymer.

In the amino acid having an immobilized functional group on a side chain, the immobilized functional group is preferably at least one selected from the group consisting of an amino group, a thiol group, and an aldehyde group, and more preferably at least one selected from the group consisting of an amino group and a thiol group.

The amino acid included in an immobilized functional group in a side chain is preferably at least one kind of amino acid selected from the group consisting of L-lysine, D-lysine, L-cysteine, D-cysteine, L-homocysteine, and D-homocysteine.

By using an amino group as an immobilized functional group, binding to a carboxy group on a carrier is possible via an amide bond, and the cyclic peptide of the present invention as an affinity ligand can be easily immobilized.

In addition, by using a thiol group as an immobilized functional group, binding to an epoxy group on a carrier is possible via a covalent bond, and the cyclic peptide of the present invention as an affinity ligand can be easily immobilized.

As the amino acid having an amino group in a side chain, there are L-lysine, D-lysine, and the like, and as the amino acid having a thiol group in a side chain, there are L-cysteine and D-cysteine. Since these are relatively less expensive and thus can suppress the synthesis cost of the cyclic peptide of the present invention, these are preferable from a viewpoint of economic efficiency.

(t and u)

In the formula (IB), t and u each are an integer that satisfies $0 \leq t \leq 5$, $0 \leq u \leq 5$, and $\leq \text{Max}(t, u) \leq 5$, preferably an integer that satisfies $0 \leq t \leq 4$, $0 \leq u \leq 4$, and $1 \leq \text{Max}(t, u) \leq 4$, and more preferably an integer that satisfies $0 \leq t \leq 3$, $0 \leq u \leq 3$, and $1 \leq \text{Max}(t, u) \leq 3$.

In a case where $t \neq u$, Max(t, u) represents the greater one out of two numbers of t and u, and in a case where $t = u$, Max(t, u) represents t or u.

(v1, v2, w1, and w2)

In the formula (IB), v1, v2, w1, and w2 are each independently an integer of 0 or more.

v1 preferably satisfies $0 \leq v1 \leq 20$, more preferably satisfies $0 \leq v1 \leq 10$, still more preferably $0 \leq v1 \leq 5$, and even more preferably $0 \leq v1 \leq 2$.

v2 preferably satisfies $0 \leq v2 \leq 20$, more preferably satisfies $0 \leq v2 \leq 10$, still more preferably $0 \leq v2 \leq 5$, and even more preferably $0 \leq v2 \leq 2$.

w1 preferably satisfies $0 \leq w1 \leq 20$, more preferably satisfies $0 \leq w1 \leq 10$, still more preferably $0 \leq w1 \leq 5$, and even more preferably $0 \leq w1 \leq 2$.

w2 preferably satisfies $0 \leq w2 \leq 20$, more preferably satisfies $0 \leq w2 \leq 10$, still more preferably $0 \leq w2 \leq 5$, and even more preferably $0 \leq w2 \leq 2$.

(Number of Amino Acid Residues of Cyclic Portion)

In the formula (IB), the number of amino acid residues [(m+n+5) residues] of the cyclic portion $[X^a\text{-}X_m\text{-}X^1\text{-}X^2\text{-}X^3\text{-}X_n\text{-}X^b]$ is 8 to 14, preferably 9 to 13, and more preferably 10 to 12, similar to the formula (I).

In a case where the number of the amino acid residues of the cyclic portion is within the range, the intramolecular strain of the cyclic peptide does not become too large and the higher-order structure such as a helix is stabilized. Therefore, the antibody binding properties of the cyclic peptide of the present invention is excellent.

(Difference Between Repeating Units in Case where $k \geq 2$)

In addition, in a case where $k \geq 2$, that is, in a case where the cyclic peptide represented by the formula (IB) contains two or more of repeating units $[X_i\text{-}X^a\text{-}X_m\text{-}X^1\text{-}X^2\text{-}X^3\text{-}X_n\text{-}X^b\text{-}X_j]$, $X^1$, $X^2$, $X^3$, $X^a$, $X^b$, $X_m$, $X_n$, $X_i$, and $X_j$ in the repeating units each may be the same, or different between the repeating units.

(Total Number of Amino Acid Residues of Cyclic Peptide)

In addition, in the formula (IB), the total number of the amino acid residues of the cyclic peptide is preferably 8 to 50, more preferably 9 to 40, still more preferably 10 to 30, and even more preferably 10 to 20.

That is, in the formula (IB), i, j, m, n, t, u, v1, v2, w1, w2, and k preferably satisfy $8 \leq (i+j+m+n+5) \times k+t+u+v1+v2+w1+w2 \leq 50$, more preferably satisfy $9 \leq (i+j+m+n+5) \times k+t+u+v1+v2+w1+w2 \leq 40$, still more preferably satisfy $10 \leq (i+j+m+n+5) \times k+t+u+v1+v2+w1+w2 \leq 30$, and even more preferably satisfy $10 \leq (i+j+m+n+5) \times k+t+u+v1+v2+w1+w2 \leq 20$.

In general, the greater the number of the amino acid residues, the higher the synthesis cost. Therefore, from a viewpoint of economic efficiency, the total number of the amino acid residues is preferably small.

<<Formula (IC)>>

In addition, the cyclic peptide is more preferably cyclic peptide represented by the following formula (IC).

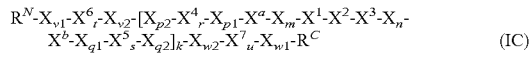

(IC)

In the formula (IC), any of $R^N$, $R^C$, $X^1$, $X^2$, $X^3$, $X^a$, $X^b$, $X_m$, $X_n$, X, m, n, and k is the same as those in the formula (I), any of $X^4$, $X^5$, p1, p2, q1, q2, r, and s is the same as those in the formula (IA), and any of $X^6$, $X^7$, t, u, v1, v2, w1, and w2 is the same as those in the formula (IB).

In addition, in the formula (IC), similar to $X_n$ in the formula (I), $X_n$ means that n Xs are linked. The same applies to $X_m$, $X_{p1}$, $X_{p2}$, $X_{q1}$, $X_{q2}$, $X_{v1}$, $X_{v2}$, $X_{w1}$, and $X_{w2}$.

In addition, in the formula (IC), $X^4_r$, $X^5_s$, $X^6_t$ and $X^7_u$ mean that r $X^4$s are linked, s $X^5$s are linked, t $X^6$s are linked, and u $X^7$s are linked, respectively.

(Cyclic Portion, Straight Chain Portion, Crosslinking Portion, and Antibody Binding Portion)

The straight chain portion of the cyclic peptide represented by the formula (IC) is "$X_{v1}$-$X^6_r$-$X_{v2}$", "$X_{w2}$-$X^7_u$-$X_{w1}$,", "$X_{p2}$-$X^4_r$-$X_{p1}$", and "$X_{q1}$-$X^5_s$-$X_{q2}$". The cyclic portion, the crosslinking portion, and the antibody binding portion are the same as those of the cyclic peptide represented by the formula (I).

In addition, in the formula (IC), similar to the formula (IA), the repeating unit is [$X_{p2}$-$X^4_r$-$X_{p1}$-$X^a$-$X_m$-$X^1$-$X^2$-$X^3$-$X_n$-$X^b$-$X_{q1}$-$X^5_s$-$X_{q2}$].

(Number of Amino Acid Residues of Cyclic Portion)

In the formula (IC), the number of amino acid residues [(m+n+5) residues] of the cyclic portion [$X^a$-$X_m$-$X^1$-$X^2$-$X^3$-$X_n$-$X^b$] is 8 to 14, preferably 9 to 13, and more preferably 10 to 12, similar to the formula (I).

In a case where the number of the amino acid residues of the cyclic portion is within the range, the intramolecular strain of the cyclic peptide does not become too large and the higher-order structure such as a helix is stabilized. Therefore, the antibody binding properties of the cyclic peptide of the present invention is excellent.

(Difference Between Repeating Units in Case where k≥2)

In addition, in a case where k≥2, that is, in a case where the cyclic peptide represented by the formula (IC) contains two or more of repeating units [$X_{p2}$-$X^4_r$-$X_{p1}$-$X^a$-$X_m$-$X^1$-$X^2$-$X^3$-$X_n$-$X^b$-$X_{q1}$-$X^5_s$-$X_{q2}$], $X^1$, $X^2$, $X^3$, $X^n$, $X^b$, $X^4_r$, $X^5_s$, $X_m$, $X_n$, $X_{p2}$, $X_{p1}$, $X_{q1}$, and $X_{q2}$ in the repeating units each may be the same, or different between the repeating units.

(Total Number of Amino Acid Residues of Cyclic Peptide)

In addition, in the formula (IC), the total number of the amino acid residues of the cyclic peptide is preferably 8 to 50, more preferably 9 to 40, still more preferably 10 to 30, and even more preferably 10 to 20.

That is, in the formula (IC), m, n, p1, p2, q1, q2, r, s, t, u, v1, v2, w1, w2, and k preferably satisfy 8≤(m+n+p1+p2+q1+q2+r+s+5)×k+t+u+v1+v2+w1+w2≤50, more preferably satisfy 9≤(m+n+p1+p2+q1+q2+r+s+5)×k+t+u+v1+v2+w1+w2≤40, still more preferably satisfy 10≤(m+n+p1+p2+q1+q2+r+s+5)×k+t+u+v1+v2+w1+w2≤30, and even more preferably satisfy 10≤(m+n+p1+p2+q1+q2+r+s+5)×k+t+u+v1+v2+w1+w2≤20.

In general, the greater the number of the amino acid residues, the higher the synthesis cost. Therefore, from a viewpoint of economic efficiency, the total number of the amino acid residues is preferably small.

<<$X_m$-$X^1$-$X^2$-$X^3$-$X_n$>>

In addition, an amino acid moiety sequence $X_m$-$X^1$-$X^2$-$X^3$-$X_n$ in the formulae (I), (IA), (IB), or (IC) preferably shares 70% or more sequence identity, more preferably shares 75% or more sequence identity, still more preferably shares 85% or more sequence identity, and even more preferably shares 90% or more sequence identity with the amino acid sequence represented by the formula (1) (SEQ ID NO: 1) or the amino acid sequence represented by the formula (2) (SEQ ID NO: 2).

(1)
A-Y-H-L$^1$-G-E-L$^2$-V-W...

(2)
A-Y-H-R-G-E-L$^2$-V-W...

In the formulae (1) and (2), A represents L-alanine residue or D-alanine residue; Y represents L-tyrosine residue or D-tyrosine residue; H represents L-histidine residue or D-histidine residue; L$^1$ represents L-leucine residue or D-leucine residue; R represents L-arginine residue or D-arginine residue; G represents glycine residue; E represents L-glutamic acid residue or D-glutamic acid residue; L$^2$ represents L-leucine residue; V represents L-valine residue; and W represents L-tryptophan residue.

Here, sequence identity of two amino acid sequences are obtained by the following manner.

(i) Alignment of Two Amino Acid Sequences is Performed.

A score of +1 is given to a match case, a score of −1 is given to a mismatch case, a score of −1 is given to a gap, and alignment is performed such that the alignment/score becomes the greatest.

(ii) Sequence Identity is Calculated.

Based on the obtained alignment, sequence identity is calculated by the following equation.

Sequence identity [%]=(number of match positions/number of all positions)×100[%]

The number of all positions is a length of alignment, and the number of match positions is the number of positions at which the kinds of amino acids are matched.

Here, whether or not the kinds of the amino acid residues are matched with one another depends on whether or not the structures of side chains (amino acid side chains) of amino acids which are sources of the amino acid residues are identical to one another. The structures of the side chains of amino acids which are in a relationship of enantiomer.

(iii) Calculation Examples of Sequence Identity

For example, the following amino acid sequences are considered.

```
Sequence A
A Y H R G E L V W

Sequence B
A W H G E L V W
```

In a case where these are aligned under the above-described conditions, the result is as follows. To sites where the kinds of amino acids (residues) are matched between Sequences A and B, for easy viewing, homology string "|" is added. In addition, "-" is a gap.

```
Sequence A     A Y H R G E L V W
               |   | | | | | |
Sequence B     A W H L G E L V W
```

The score of this alignment is match (+1)×7+mismatch (−1)×1+gap (−1)×1=5.

In this example, since the number of all positions is 9, and the number of match positions is 7, the sequence identity calculated according to the formula is 7/9×100=77.8%.

In the present invention, in the formulae (I) to (IC), preferably k=1.

In a case where the repeating unit is 1, in a case where it is possible to shorten the total length of the cyclic peptide, synthesis becomes easy. In addition, it is possible to prevent crosslinking at unintended sites from being formed by Huisgen reaction at the time of cyclization.

The cyclic peptide is particularly preferably a cyclic peptide represented by the following formula (II).

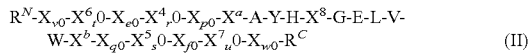

(II)

In the formula (II), $X^a$, $X^b$, X, $R^N$, and $R^C$ are the same as those in the formula (I).

In addition, in the formula (II), similar to $X_n$ in the formula (I), $X_{e0}$ means that e0 Xs are linked. The same applies to $X_{f0}$, $X_{p0}$, $X_{q0}$, $X_{v0}$, and $X_{w0}$.

The cyclic portion of the cyclic peptide represented by the formula (II) is "$X^a$-A-Y-H-$X^8$-G-E-L-V-W-$X^b$", the straight chain portion is "$X_{v0}$-$X^6_{f0}$-$X_{e0}$-$X^4_{f0}$-$X_{p0}$-" and "$X_{q0}$-$X^5_{s0}$-$X_{f0}$-$X^7_{u0}$-$X_{w0}$", the crosslinking portion is "$X^a$" and "$X^b$", and the antibody binding portion is "L-V-W".

In the formula (II), $X^4$ and $X^5$ are the same as those in the formula (IA).

In the formula (II), $X^6$ residue derived from f-azide-L-alanine, and Xaa1 and Xaa11 form a triazole bond between a propargyl group of a side chain of 2-propargyl-L-homoglycine and an azide group of a side chain of β-azide-L-alanine to crosslink thereof (SEQ ID NO: 9).

-Xaa1-Ala-Tyr-His-Arg-Gly-Glu-Leu-Val-Trp-Xaa11- (viii)

In the formula (viii), Xaa1 is an amino acid residue derived from f3-azide-L-alanine, Xaa11 is an amino acid residue derived from 2-propargyl-L-homoglycine, and Xaa1 and Xaa11 form a triazole bond between an azide group of a side chain of β-azide-L-alanine and a propargyl group of a side chain of 2-propargyl-L-homoglycine to crosslink thereof (SEQ ID NO: 10).

(Those Crosslinked by Amide Bond)

-Xaa1-Ala-Tyr-His-Leu-Gly-Glu-Leu-Val-Trp-Xaa11- (ix)

In the formula (ix), Xaa1 is an amino acid residue derived from L-lysine, Xaa1 is an amino acid residue derived from L-glutamic acid, and Xaa1 and Xaa11 form an amide bond between an amino group of a side chain of L-lysine and a carboxy group of a side chain of L-glutamic acid to crosslink thereof (SEQ ID NO: 11).

-Xaa1-Ala-Tyr-His-Leu-Gly-Glu-Leu-Val-Trp-Xaa11- (x)

In the formula (ix), Xaa1 is an amino acid residue derived from L-glutamic acid, Xaa11 is an amino acid residue derived from L-lysine, and Xaa1 and Xaa11 form an amide bond between a carboxy group of a side chain of L-glutamic acid and an amino group of a side chain of L-lysine to crosslink thereof (SEQ ID NO: 12).

<<Affinity Ligand Introduction Amount>>

The amount of the affinity ligand to be introduced into the mixed mode affinity chromatography carrier of the present invention (hereinafter, sometimes simply referred to as "affinity ligand introduction amount") is not particularly limited, but it is preferably 0.01 mmol/L-gel to 100 mmol/L-gel, more preferably 0.05 mmol/L-gel to 50 mmol/L-gel, still more preferably 0.10 mmol/L-gel to 10 mmol/L-gel, even more preferably 0.10 mmol/L-gel to 5.0 mmol/L-gel, and even still more preferably 0.10 mmol/L-gel to 2.5 mmol/L-gel.

<<Synthesis Method of Cyclic Peptide>>

A synthesis method of the cyclic peptide is not particularly limited, and for example, synthesis is possible by an organic synthetic chemical peptide synthesis method or a gene engineering peptide synthesis method.

As the organic synthetic chemical peptide synthesis method, any of a liquid phase synthesis method and a solid phase synthesis method can be used. As the synthesis method of polypeptide of the present invention, the solid phase synthesis method using an automatic peptide synthesis apparatus is convenient and thus preferable.

The gene engineering peptide synthesis method is a method of introducing genes into a cell and synthesizing peptide. As the cell, bacteria, nematode cell, insect cell, mammalian cell, and animal cell can be used.

For example, it is possible to introduce an unnatural amino acid to perform synthesis by using a 4-base codon method. In addition, it is possible to perform cyclization and synthesis by synthesizing a straight chain peptide and reacting thereof with a crosslinking functional group of a side chain of an amino acid residue introduced into the cyclic portion.

In a case of forming a disulfide bond, for example, it is possible to form a disulfide bond by reacting side chain thiol groups of homocysteine residues with each other or reacting a side chain thiol group of a homocysteine residue with a side chain thiol group of an amino acid residue having a longer methylene chain than homocysteine under an oxidizing condition.

In a case of forming a thioether bond, for example, it is possible to form a thioether bond by reacting a lysine residue obtained by chloroacetylating an amino group of a side chain or an orthenine residue with a side chain thiol group of a homocysteine residue.

Since a thioether bond is formed by chlororizing a side chain amino group of a lysine residue by chloroacetylation ($-NH-C(=O)-CH_2-Cl$; number of methylene unit 1) or 3-chloropion oxidation ($-NH-C(=O)-(CH_2)_2-Cl$; number of methylene unit 2), and then reacting thereof with a thiol group, compounds used in chlororization are not limited to those exemplified here. However, as the number of methylene units is small, that is, as the methylene chain is short, cyclization efficiency becomes high, and thus those with small number of methylene units are preferable.

In a case of forming a triazole bond, for example, as a crosslinking functional group, an azide group and an alkynyl group are used. In synthesizing a polypeptide chain including an amino acid residue obtained by introducing an azide group or an alkynyl group, there is a method of incorporating an amino acid obtained by introducing an azide group or an alkynyl group into a polypeptide chain at the time of peptide synthesis or a method of synthesizing a polypeptide chain, and then introducing an azide group or an alkynyl group into a side chain of a desired amino acid residue. Any of the methods may be used.

After synthesizing the polypeptide chain including the amino acid residue obtained by introducing an azide group or an alkynyl group, addition reaction between the alkynyl group and the azide group is caused by Huisgen reaction to perform crosslinking between amino acid residues. Huisgen reaction is 1,3-dipole addition cyclization reaction of forming 1,2,3-triazole from azide (compound having a $-N=N^+=N^-$ atomic group) and alkyne (carbon-carbon triple bond compound). The azide group and the alkynyl group are inert with respect to many functional groups or living body molecules, and reaction generating triazole ring from both of the azide group and the alkynyl group is thermodynamically advantageous reaction. Since the Huisgen reaction dramatically accelerates in the presence of a copper catalyst, it is preferable to use a copper catalyst.

<Cation Exchange Group>

Since a cation exchange group cooperatively acts with an antibody-binding cyclic peptide, and has a specific adsorption function and an aggregate removal function, it is considered that the cation exchange group improves an impurities removal function of the mixed mode affinity chromatography carrier of the present invention.

The cation exchange group used in the mixed mode affinity chromatography carrier of the present invention is not particularly limited, but preferably a carboxy group or a sulfoxy group, and more preferably a carboxy group. Any of the carboxy group and the sulfoxy group is excellent in aggregate removal function. However, the carboxy group has weaker ionic strength than the sulfoxy group and can suppress non-specific adsorption to be low, and thus is particularly advantageous.

<<Cation Exchange Group Introduction Amount>>

The amount of the cation exchange group to be introduced into the mixed mode affinity chromatography carrier of the present invention (hereinafter, sometimes simply referred to as "cation exchange group introduction amount") is not particularly limited, but preferably 15 mmol/L-gel to 60 mmol/L-gel, more preferably 15 mmol/L-gel to 55 mmol/L-gel, and still more preferably 15 mmol/L-gel to 40 mmol/L-gel in terms of ion exchange capacity.

In the case where the cation exchange group introduction amount is within this range, the affinity ligand introduction amount can be set within an appropriate range, and therefore adsorption of non-specific adsorbates can be suppressed.

[Method for Producing Mixed Mode Affinity Chromatography Carrier]

The mixed mode affinity chromatography carrier of the present invention can be produced by coating a substrate with a hydrophilic polymer, introducing a cation exchange group, and introducing an affinity ligand into at least one of the substrate or the hydrophilic polymer.

Details of the substrate, the hydrophilic polymer, and the affinity ligand are as described in the section "Mixed mode affinity chromatography carrier".

(1) The Substrate is Coated with a Hydrophilic Polymer.

The method of coating the substrate with a hydrophilic polymer is not particularly limited as long as it is capable of binding the hydrophilic polymer to the substrate by a covalent bond. Examples of the method of coating the substrate with a hydrophilic polymer include a method in which a substrate is reacted with 2-chloromethyloxirane (another name: epichlorohydrin) to introduce an epoxy group into the substrate which is then reacted with a hydrophilic polymer; a method in which a substrate is reacted with a crosslinking agent such as 2-chloromethyloxirane (another name: epichlorohydrin) in the presence of an alkali in a solvent, and the resulting reaction product is reacted with a hydrophilic polymer; and a method in which a halogen group (halogen atom) such as a chloro group (chlorine atom) is introduced into a substrate using a halogenating agent and a hydrophilic polymer is immobilized on the substrate using a Williamson ether synthesis method.

In the case where the substrate is coated with the hydrophilic polymer, the hydrophilic polymer coating amount is preferably 3 mg/g-dry gel to 450 mg/g-dry gel, more preferably 3 mg/g-dry gel to 250 mg/g-dry gel, still more preferably 3 mg/g-dry gel to 230 mg/g-dry gel, even more preferably 10 mg/g-dry gel to 230 mg/g-dry gel, and even still more preferably 20 mg/g-dry gel to 230 mg/g-dry gel.

In the present specification, a substrate immediately before coating with a hydrophilic polymer is sometimes referred to as "substrate before coating" in some cases, and a product obtained by coating such a substrate before coating with a hydrophilic polymer is sometimes referred to as "coated carrier" in some cases.

(2) A Cation Exchange Group is Introduced into a Coated Carrier.

The method of introducing a cation exchange group into the coated carrier is not particularly limited as long as it is capable of binding a compound having a cation exchange group to the coated carrier by a covalent bond. Examples of the method of introducing a cation exchange group into the coated carrier include a method in which a coated carrier is reacted with chloroacetic acid under alkaline conditions and a carboxymethyl group is introduced into a part of hydroxy groups on the surface of the coated carrier; and a method in which a formyl group is introduced into a coated carrier, and a cation exchange group is introduced into the formyl group by reductive amination through an amino group of a compound having a cation exchange group and an amino group such as amino acid.

In the case of introducing a cation exchange group into the coated carrier, the cation exchange group introduction amount is 15 mmol/L-gel to 60 mmol/L-gel, preferably 15 mmol/L-gel to 55 mmol/L-gel, and more preferably 15 mmol/L-gel to 40 mmol/L-gel in terms of ion exchange capacity.

In the present specification, the product obtained by introducing a cation exchange group into the coated carrier is sometimes referred to as "cation exchange group-introduced carrier" in some cases. In particular, the product obtained by introducing a carboxy group into the coated carrier is sometimes referred to as "carboxy group-introduced carrier", and the product obtained by introducing a sulfoxy group into the coated carrier is sometimes referred to as "sulfoxy group-introduced carrier".

(3) An Affinity Ligand is Introduced (Immobilized) into the Cation Exchange Group-Introduced Carrier.

The method of introducing (immobilizing) an affinity ligand into the cation exchange group-introduced carrier is not particularly limited as long as it is capable of binding the affinity ligand to the cation exchange group-introduced carrier by a covalent bond. Examples of the method of introducing (immobilizing) an affinity ligand into the cation exchange group-introduced carrier include a method in which a part of cation exchange groups is converted into N-(3-dimethylaminopropyl)-N'-ethylcarbodiimide (EDC)/N-hydroxysuccinimide (NHS) and reacted with an affinity ligand, and the unreacted EDC/NHS-converted cation exchange group is regenerated after the reaction; and a method in which, in the case of an affinity ligand having an amino group, a cation exchange group is protected, a formyl group is introduced, and then the affinity ligand is introduced into the formyl group by reductive amination through an amino group.

In the case where the affinity ligand is introduced into the cation exchange group-introduced carrier, the affinity ligand introduction amount is preferably 0.01 mmol/L-gel to 100 mmol/L-gel, more preferably 0.05 mmol/L-gel to 50 mmol/L-gel, still more preferably 0.10 mmol/L-gel to 10 mmol/L-gel, even more preferably 0.10 mmol/L-gel to 5.0 mmol/L-gel, and even still more preferably 0.10 mmol/L-gel to 2.5 mmol/L-gel.

In the case where the affinity ligand binds to a part of the cation exchange group of the cation exchange group-introduced carrier, the amount of the cation exchange group introduced into the mixed mode affinity chromatography carrier is expressed by "amount of cation exchange group introduced into cation exchange group-introduced carrier—amount of affinity ligand introduced into mixed mode affinity chromatography carrier".

[Method for Purifying Biological Substance and Biological Substance Purified by Same Purification Method]

The biological substance to be purified by the mixed mode affinity chromatography carrier of the present invention is not particularly limited, but it is preferably an antibody or an antibody derivative and more preferably immunoglobulin G or a derivative thereof.

These are used as a raw material of antibody drugs.

Hereinafter, a detailed description of the purification method using the mixed mode affinity chromatography carrier of the present invention is exemplified for the case where the biological substance is immunoglobulin G, but the present invention is not limited thereto.

The purification of a biological substance (in particular, an antibody) using a mixed mode affinity chromatography carrier is largely composed of four steps of an adsorption step, a washing step, an ionic strength adjusting step, and an elution step, and may include subsequent steps for re-use such as a regeneration step and/or a cleaning-in-place (CIP) step, and a re-equilibration step.

In the adsorption step, a general affinity chromatography purification method can be used. That is, in one example, the pH of a protein solution containing immunoglobulin G is adjusted to near neutral pH and then the solution is passed through a column packed with the mixed mode affinity chromatography carrier of the present invention, so that the immunoglobulin G is specifically adsorbed on the mixed mode affinity chromatography carrier through an affinity ligand. For example, in the case where antibody-binding cyclic peptide is used as the affinity ligand, the loading pH, that is, the pH at the time of adding a biological substance is preferably 5.0 to 9.0, more preferably 5.3 to 9.0, still more preferably 5.5 to 9.0, and even more preferably 6.0 to 8.5. In the purification of immunoglobulin G produced by cultured mammalian cells, it is not necessary to specifically adjust the ionic strength, and it is also possible to further suppress the non-specific adsorption by increasing the ionic strength in advance.

In the washing step, an appropriate amount of a buffer solution within the range of conditions in which the affinity ligand functions is allowed to pass, so that the interior of the column is washed. That is, the preferred range of the pH of the buffer solution may be the same range as that at the time of loading. For example, it is preferably a pH of 5.0 to 9.0. At this point, the immunoglobulin G is adsorbed on the mixed mode affinity chromatography carrier of the present invention. In this case, impurities may be effectively removed by optimizing ionic strength and/or composition at a pH near neutral. It is preferred that the cation exchange group does not function at the time of washing, that is, it is preferable to use a washing solution having a certain ionic strength or more at a pH near neutral, and in this process, it is possible to wash impurities non-specifically remaining in the column through the mixed mode affinity chromatography carrier and/or the immunoglobulin G. The ionic strength is, for example, preferably 0.2 M or more and more preferably 0.5 M or more.

In the ionic strength adjusting step, the column is replaced with a buffer solution having a low ionic strength near neutrality to prepare for the expression of an ionic strength-dependent elution function by the cation exchange group at the time of elution.

In the elution step, the combination of acidic pH and ionic strength allows the cation exchange separation mode to function at the time of elution from the affinity ligand, and therefore a fraction having a high monomer content can be recovered into a low ionic strength elution fraction by the cooperative action of both ligands. As for the pH of the eluate, the pH at the time of elution of immunoglobulin G from the affinity ligand can be applied. Since this pH is determined mainly by the separation conditions determined by the mixed mode affinity chromatography carrier and the type of immunoglobulin G, it is not necessary to set special conditions.

The pH at the time of elution is preferably set to 2.0 to 5.0. However, for the purpose of avoiding acid denaturation of the biological substance, the pH is more preferably pH 2.8 or more, still more preferably pH 3.0 or more, and even more preferably pH 3.2 or more. The pH is preferably 5.0 or less and more preferably 4.8 or less.

In the case where an alkaline-resistant cyclic peptide is used as the affinity ligand, the pH at the time of elution is generally set to preferably 3.2 to 4.0, but it is not limited thereto. In addition, the elution ionic strength depends on the introduction ratio of the affinity ligand and the cation exchange group and also depends on the loading amount of immunoglobulin G per unit volume, but the optimization point thereof can be easily set by gradient experiment or stepwise elution experiment.

The antibody elution from the mixed mode affinity chromatography carrier prepared according to the present invention can be applied either by salt concentration gradient elution or stepwise elution, but in the case of aiming to reduce the amount of eluate, stepwise elution by ionic strength is preferable. Further, in order to simplify the operation, it is preferable to set the conditions that can achieve recovery and high purification purity of antibodies by one step elution.

Even with a combination of ionic strength and acidic pH in the washing step, in the case where the aggregate remains in the column and is not mixed into the eluted fraction, the ionic strength adjusting step can be omitted.

The biological substance purified according to the purification method of the present invention, particularly an antibody or an antibody derivative, exhibits an increased purification purity although the structure and properties of the biological substance are not changed before and after purification thereof. However, since the purification purity depends on the solution or the like before purification, it is impossible to say unconditionally how high the purification purity is.

The immunoglobulin G purified using the mixed mode affinity chromatography carrier prepared according to the present invention exhibits a higher monomer selectivity than affinity chromatography carrier based on a single separation mode and a high content of monomers in the eluate.

Even in the case where an affinity chromatography carrier based on a single separation mode is used, it is possible to increase the monomer content to some extent by optimization of pH at the time of elution and ionic strength, but such an effect is low and it is accompanied by a greater decrease in recovery rate for exhibiting the effect. By using the mixed mode affinity chromatography carrier of the present invention, since affinity purification with high specificity and improvement in monomer content that can be achieved mainly by cation exchange chromatography can be achieved with efficiency in a single chromatographic operation while maintaining a high recovery rate, it is possible to reduce the load on subsequent processes, which is therefore capable of contributing to improvement of the yield of the entire process and improvement of the monomer content. That is, the use of the novel mixed mode affinity chromatography carrier of the present invention can contribute to improvement in productivity and purification of the antibody drug production process.

EXAMPLES

Hereinafter, the present invention will be described in more detail with reference to Examples, but the present invention is not limited thereto.

[Measurement Method and Evaluation Method]

A. Method for Measuring Cation Exchange Group Introduction Amount 1 g of the carboxylated carrier was suspended in 3 mL of pure water, the resulting suspension was poured into a disposable column having an inner diameter of 15 mm, and the solvent was removed by suction filtration. This was followed by washing 4 times with 3 mL of 0.2 mol/L hydrochloric acid and then repeated washing with 4 mL of pure water. After washing, the height of the bed (carrier part deposited on the column) was measured to calculate the volume of the carboxylated carrier. The carboxylated carrier was taken out, transferred to a 100 mL beaker, suspended in 40 mL of 0.1 mol/L saline, and titrated with a 0.1 mol/L aqueous sodium hydroxide solution using an automatic titrator "COM-1600" (manufactured by Hiranuma Sangyo Co., Ltd.). The ion exchange capacity (meq/L-gel) per 1 L of the carboxylated carrier was calculated from the amount of the titration solution up to the end point. Further, the unit was converted into "mmol/L-gel" (1 meq/L-gel=1 mmol/L-gel). The cation exchange group introduction amount was expressed in terms of ion exchange capacity.

B. Method for Measuring Affinity Ligand Introduction Amount (Peptide Immobilization Amount)

The peptide solution, the reaction solution, and the washing solution after the peptide immobilization reaction were each subjected to gel filtration chromatography (which will be described below), and the amount of peptide contained in each solution was calculated from the peak surface area value of absorbance at 280 nm.

The peptide immobilization amount was calculated from the difference between the amount of peptide contained in the peptide solution, the reaction solution, and the washing solution before the peptide immobilization reaction.

(Conditions for Gel Filtration Chromatography)

Chromatographic system: AKTA avant 25 (manufactured by GE Healthcare GmbH) ("AKTAAVANT" is a registered trademark)

Column: Gel filtration chromatography column for peptide purification "Superdex Peptide 10/300 GL (manufactured by GE Healthcare GmbH)"

Buffer: 20 mM phosphate buffer, 150 mM NaCl, pH 7.4

Flow rate: 0.5 mL/min

C. Evaluation Method of Antibody Adsorption Capacity (a) Measurement of Antibody Adsorption Capacity 1 mL of a mixed mode affinity chromatography carrier produced in Examples and Comparative Examples was packed in a glass column "TRICORN 10/20 column" (manufactured by GE Healthcare GmbH) ("TRICORN" is a registered trademark) which was then connected to a chromatographic system "AKTA avant 25" (manufactured by GE Healthcare GmbH) ("AKTAAVANT" is a registered trademark), followed by the measurement of antibody adsorption capacity.

After the column was equilibrated with an equilibration solution (20 mM phosphate buffer, 150 mM NaCl, pH 7.4), 15 mL of a solution prepared by adjusting a human IgG antibody (Immunoglobulin G) to 5 mg/mL with standard buffer (20 mM phosphate buffer, 150 mM NaCl, pH 7.4) was added thereto at a flow rate of 0.42 mL/min. After washing the column with 5 mL of a post-loading washing solution (20 mM phosphate buffer, 150 mM NaCl, pH 7.4) at the same flow rate, 5 mL of a pre-elution washing solution (20 mM phosphate buffer, 1 M NaCl, pH 7.4) was allowed to flow at the same flow rate. Thereafter, 5 mL of an eluate (100 mM citrate buffer, 500 mM NaCl, pH 3.2) was allowed to flow at the same flow rate. Further continuously, 5 mL of a cleaning in place (CIP) solution (0.1 M aqueous sodium hydroxide solution) was allowed to flow at the same flow rate and then 5 mL of a re-equilibration solution (20 mM phosphate buffer, 150 mM NaCl, pH 7.4) was allowed to flow at the same flow rate. At this time, the antibody elution amount of the eluate in each fraction was calculated from the IgG elution peak obtained by monitoring the absorbance at 280 nm. The amount of antibodies eluted from the pre-elution washing solution to the CIP solution was calculated as the antibody adsorption capacity.

(b) Evaluation of Antibody Adsorption Capacity

The antibody adsorption capacity was evaluated based on the following criteria.

Antibody adsorption capacity is greater than 30 g/L . . . Evaluation "A"

Antibody adsorption capacity is greater than 3.5 g/L and equal to or less than 30 g/L . . . Evaluation "B"

Antibody adsorption capacity is equal to or less than 3.5 g/L . . . Evaluation "E"

Evaluations A and B represent that the antibody adsorption capacity is sufficient, and Evaluation E represents that the antibody adsorption capacity is not sufficient.

In a case where the mixed mode affinity chromatography carrier of the present invention having sufficient antibody adsorption capacity is used in purification of antibodies, it is possible to increase the purification efficiency of the antibodies and to further decrease the antibody purification cost.

D. Evaluation Method of Impurities Removal Function (a) Calculation of HCP Purification Factor 1 mL of a mixed mode affinity chromatography carrier produced in Examples or Comparative Examples was packed in a glass column "TRICORN 10/20 column" (manufactured by GE Healthcare GmbH) ("TRICORN" is a registered trademark) which was then connected to a chromatographic system "AKTA avant 25" (manufactured by GE Healthcare GmbH) ("AKTAAVANT" is a registered trademark), followed by the measurement of the amount of host cell protein (HCP) and the amount of Immunoglobulin G (IgG) eluted from each fraction.

(Measurement of IgG Amount and HCP Amount)

After the column was equilibrated with an equilibration solution (20 mM phosphate buffer, 150 mM NaCl, pH 7.4), an IgG/HCP mixed solution prepared by using standard buffer (20 mM phosphate buffer, 150 mM NaCl, pH 7.4), so that IgG and HCP derived from a Chinese Hamster Ovary S (CHO-S) cell were 1.6 mg/mL and 0.32 mg/mL, respectively, was added at a flow rate of 0.21 mL/min such that an antibody amount of 80% of the antibody adsorption capacity obtained in the above C was loaded. After washing the column with 5 mL of a post-loading washing solution (20 mM phosphate buffer, 150 mM NaCl, pH 7.4) at a flow rate of 0.42 mL/min, 5 mL of a pre-elution washing solution (20 mM phosphate buffer, 1 M NaCl, pH 7.4) was allowed to flow at the same flow rate. Thereafter, 5 mL of an ionic strength adjusting solution (20 mM phosphate buffer, pH 7.4) was allowed to flow at the same flow rate. Thereafter, 5 mL of an eluate 1 (100 mM citrate buffer, pH 3.2) was allowed to flow at the same flow rate, further continuously 5 mL of an eluate 2 (100 mM citrate buffer, 50 mM NaCl, pH 3.2), 5 mL of an eluate 3 (100 mM citrate buffer, 75 mM NaCl, pH 3.2), and 5 mL of an eluate 4 (100 mM citrate buffer, 500 mM) were allowed to flow at the same flow rate. Further continuously, 5 mL of a CIP solution (0.1 M aqueous sodium hydroxide solution) was allowed to flow at the same flow rate and then 5 mL of a re-equilibration solution (20 mM phosphate buffer, 150 mM NaCl, pH 7.4) was allowed to flow at the same flow rate.

The IgG elution amount of the eluate in each fraction was calculated from the IgG elution peak obtained by monitoring the absorbance at 280 nm.

The eluate of each fraction was recovered, the pH of each eluate was set at 5 to 6 using 1 M Tris-HCl solution, and then the amount of HCP of the eluate in each fraction was calculated by ELISA using a host cell protein detection kit "CHO HCP 3rd Generation ELISA kit" (manufactured by Cygnus Technologies, Inc.).

(Calculation of HCP Purification Factor)

Using the thus calculated IgG amount and HCP amount of the eluate, the HCP incorporation amount in the eluate was calculated by the following equation as the HCP amount per the IgG amount in the eluate.

HCP incorporation amount of eluates 1 to 3 (ppm)=total HCP amount of eluates 1 to 3/total IgG amount of eluates 1 to 3

HCP purification factor was calculated by the following equation from the HCP incorporation amount of the eluates (ppm) and the HCP incorporation amount of the loaded IgG/HCP mixed solution (ppm).

HCP purification factor=HCP incorporation amount of the loaded IgG/HCP mixed solution (ppm)/HCP incorporation amount of eluates 1 to 3 (ppm)

(b) Evaluation of Impurities Removal Function

The impurities removal function was evaluated based on the following criteria.

The HCP purification factor is greater than 5,000 . . . Evaluation "A"

The HCP purification factor is greater than 1,500 and equal to or less than 5,000 . . . Evaluation "B"

The HCP purification factor is equal to or less than 1,500 . . . Evaluation "E"

Evaluations A and B represent that impurities removal function is sufficient, and Evaluation E represents that impurities removal function is not sufficient.

In a case where the mixed mode affinity chromatography carrier of the present invention having sufficient impurities removal function is used in purification of antibodies, it is possible to increase purification purity of the antibodies and to further improve the purification purity of the antibodies.

E. Evaluation Method of Drug Resistance (a) Calculation of Binding Amount Change Rate 1 mL of a mixed mode affinity chromatography carrier produced in Examples or Comparative Examples was packed in a glass column "TRICORN 10/20 column" (manufactured by GE Healthcare GmbH) ("TRICORN" is a registered trademark) which was then connected to a chromatographic system "AKTA avant 25" (manufactured by GE Healthcare GmbH) ("AKTAAVANT" is a registered trademark), followed by the measurement of the amount of the antibody binding capacity. After the column was equilibrated with an equilibration solution (20 mM phosphate buffer, 150 mM NaCl, pH 7.4), 15 mL of a solution obtained by adjusting a human IgG antibody to 5 mg/mL by using a standard buffer (20 mM phosphate buffer, 150 mM NaCl, pH 7.4) was added at a flow rate of 0.21 mL/min. After washing the column with 5 mL of a post-loading washing solution (20 mM phosphate buffer, 150 mM NaCl, pH 7.4) at the same flow rate, 5 mL of a pre-elution washing solution (20 mM phosphate buffer, 1 M NaCl, pH 7.4) was allowed to flow at the same flow rate. Thereafter, 5 mL of an eluate (100 mM citrate buffer, pH 3.2) was allowed to flow at the same flow rate. Further continuously, 5 mL of a cleaning in place (CIP) solution (0.1 M sodium hydroxide) was allowed to flow at the same flow rate and then 5 mL of a re-equilibration solution (20 mM phosphate buffer, 150 mM NaCl, pH 7.4) was allowed to flow at the same flow rate. At this time, by the Immunoglobulin G (IgG) elution peak obtained by monitoring the absorbance at 280 nm, the amount of the antibody bonded to the carrier until 10% of the antibody undiluted solution leaked from the carrier was measured as the antibody binding capacity. Subsequently, after filling the mixed mode affinity chromatography carrier in 0.2 M NaOH aqueous solution at 25° C. for 6 hours and leaving still, the antibody binding capacity of the carrier was measured in the same manner, and the binding amount change rate was calculated from the antibody binding capacity before and after alkali treatment.

(b) Evaluation of Drug Resistance

Drug resistance was evaluated based on the following criteria.

Binding amount change rate is greater than 75% . . . AAA

Binding amount change rate is greater than 65% and equal to or less than 75% . . . AA Binding amount change rate is greater than 40% and equal to or less than 65% . . . A Binding amount change rate is greater than 15% and equal to or less than 40% . . . B Binding amount change rate is equal to or less than 15% . . . E Evaluations AAA, AA, A, and B represent that drug resistance is sufficient, and Evaluation E represents that drug resistance is not sufficient.

In a case where the mixed mode affinity chromatography carrier of the present invention having sufficient drug resistance is used in purification of antibodies, the carrier can specifically repetitively bind to an antibody even after washing, it is possible to purify antibodies for a long period of time, and it is possible to further decrease the antibody purification cost.

F. Evaluation Method of Antigenic Ligand Incorporation

Antigenic ligand incorporation was evaluated based on the following criteria.

Introduced affinity ligand has low antigenicity (molecular weight of less than 4,000) . . . Evaluation "A"

Introduced affinity ligand has low antigenicity (molecular weight of less than 5,000) . . . Evaluation "B"

Introduced affinity ligand has antigenicity (molecular weight of equal to or more than 5,000) . . . Evaluation "E"

Evaluations A and B represent that antigenic ligand is substantially not incorporated into the purified antibody, and Evaluation E represents that there is a concern that antigenic ligand is incorporated into the purified antibody.

In a case where an antibody into which the antigenic ligand is incorporated is administered to a living body, unexpected immune response may be derived, and there is a concern that unpreferable side effects may be caused.

Example 1

1. Production of Mixed Mode Affinity Chromatography Carrier (1) Preparation of Wet Gel The crosslinked agarose-based substrate, Sepharose 4 Fast Flow (manufactured by GE Healthcare GmbH) ("SEPHAROSE" is a registered trademark) was washed on a glass filter by repeating suspension and filtration using pure water, thereby obtaining a substrate slurry. The pure water was removed from the substrate slurry by suction filtration to obtain a wet gel.

(2) Preparation of Substrate Before Coating—Introduction of Epoxy Group 50 g of the obtained wet gel, 76 mL of pure water and 25 g of 2-chloromethyl oxirane were placed in a 300 mL three-neck flask and stirring of the contents of the flask was started in a warm bath at 45° C. Stirring was carried out until the temperature in the flask reached 45° C. 20.4 g of a 50% (w/w) aqueous sodium hydroxide solution was added dropwise in the flask over 2 hours in a warm bath at 45° C. while maintaining the temperature in the flask at about 45° C. After the whole amount of the aqueous sodium hydroxide solution was added dropwise, the mixed solution was further reacted for 1 hour and washed on a glass filter by repeating suspension and filtration using pure water to obtain a wet gel of the substrate before coating.

(3) Preparation of Carrier—Coating with Hydrophilic Polymer 31 g of dextran 40 (weight-average molecular weight: about 40,000) and 72 mL of pure water were placed in a 300 mL three-neck flask and stirring of contents of the flask was started at room temperature. Stirring was carried out until the dextran 40 was completely dissolved. After dissolution, 42 g of the wet gel of the substrate before coating was added to the three-neck flask which was then further stirred at room temperature. After the mixed solution in the three-neck flask became homogeneous, 2.0 g of a 50% (w/w) aqueous sodium hydroxide solution was added thereto. After adding the aqueous sodium hydroxide solution, the mixed solution was reacted at room temperature for 16 hours and washed on a glass filter by repeating suspension and filtration using pure water to obtain a wet gel of the carrier.

(4) Preparation of Carboxylated Carrier—Introduction of Cation Exchange Group 15 g of the wet gel of the obtained carrier, 5.1 g of sodium chloroacetate and 31 mL of pure water were placed in a 100 mL three-neck flask and stirring of the contents of the flask was started in a warm bath at 50° C. Stirring was carried out until the sodium chloroacetate was completely dissolved. After dissolution, 11 g of a 50% (w/w) aqueous sodium hydroxide solution was added dropwise over 1 hour in a warm bath at 50° C. while maintaining the temperature in the flask at about 50° C. After the whole amount of the aqueous sodium hydroxide solution was added dropwise, the mixed solution was further reacted for 3 hours and washed on a glass filter by repeating suspension and filtration using pure water to obtain a wet gel of the carboxylated carrier.

(5) Preparation of Cyclic Peptide-Immobilized Carboxylated Carrier—Introduction of Cyclic Peptide The obtained carboxylated carrier was placed in a disposable column in an amount of 2.5 mL as a wet volume and washed by repeating suspension and filtration using pure water to obtain a carrier slurry. The pure water was removed from the carrier slurry by suction filtration to obtain a wet gel.

2.0 g of the obtained wet gel was placed in a reaction vessel and 2 mL of a solution of N-(3-dimethylaminopropyl)-N'-ethylcarbodiimide (EDC) was added thereto. The mixed solution was stirred with inversion of the reaction vessel at room temperature for 10 minutes. Thereafter, 2 mL of a solution of N-hydroxysuccinimide (NHS) was added to the reaction vessel which was then stirred with inversion thereof at room temperature for 30 minutes. Here, the EDC solution was prepared by dissolving 0.2 g of EDC in 2 mL of dimethyl sulfoxide (DMSO), and the NHS solution was prepared by dissolving 0.2 g of NHS in 2 mL of DMSO.

The reaction gel solution was transferred to a disposable column and washed with 6 mL of ice-cooled 1 mM hydrochloric acid to obtain an EDC/NHS activated carboxylated carrier.

1.5 g of the obtained EDC/NHS activated carboxylated carrier was placed in a reaction vessel, followed by addition of 1.5 mL of a 5 mg/gL cyclic peptide A solution to the reaction vessel and shaking at 25° C. for 2 hours.

Here, the 5 mg/mL cyclic peptide A solution was prepared by dissolving the cyclic peptide A represented by the following formula (A) (SEQ ID NO: 13) in DMSO.

Lys-Lys-Lys-Asp-Xaa5-Ala-Tyr-His-Leu-Gly-Glu-
Leu-Val-Trp-Xaa15-Thr                 (A)

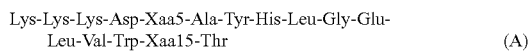

In the formula (A), Xaa5 is an amino acid residue derived from N-ε-chloroacetyl-L-lysine, Xaa15 is an amino acid residue derived from L-homocysteine, and Xaa5 and Xaa15 form a thioether bond between a chloroacetyl group of a side chain of N-ε-chloroacetyl-L-lysine and a thiol group of a side chain of L-homocysteine to crosslink thereof.

Subsequently, the solvent was replaced with a 1 M aqueous sodium chloride solution and a 0.5 M aqueous ethanolamine solution, followed by washing to obtain a cyclic peptide-immobilized carboxylated carrier.

2. Measurement of Carboxy Group Introduction Amount

A carboxy group introduction amount of the obtained carboxylated carrier was measured by the above-described "Measurement method of cation exchange group introduction amount". As a result, the carboxy group introduction amount was 30 mmol/L-gel.

3. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.7 mmol/L-gel.

4. Evaluation of Antibody Adsorption Capacity

Antibody adsorption capacity of the obtained cyclic peptide-immobilized carboxylated carrier was evaluated by the above-described "Evaluation method of antibody adsorption capacity". The evaluation result is shown in the section "Antibody adsorption capacity" in Table 3.

5. Evaluation of Impurities Removal Function

Impurities removal function of the obtained cyclic peptide-immobilized carboxylated carrier was evaluated based on the above-described "Evaluation method of impurities removal function". The evaluation result is shown in the section "Impurities removal function" in Table 3.

6. Evaluation of Drug Resistance

Drug resistance of the obtained cyclic peptide-immobilized carboxylated carrier was evaluated based on the above-described "Evaluation method of drug resistance". The evaluation result is shown in the section "Drug resistance" in Table 3.

7. Evaluation of Antigenic Ligand Incorporation

Antigenic ligand incorporation of the obtained cyclic peptide-immobilized carboxylated carrier was evaluated based on the above-described "Evaluation method of antigenic ligand incorporation". As a result, evaluation of the antigenic ligand incorporation was "A".

Example 2

1. Production of Mixed Mode Affinity Chromatography Carrier

A cyclic peptide-immobilized carboxylated carrier was prepared in the same manner as that of Example 1, except that cyclic peptide B represented by the formula (B) (SEQ ID NO: 14) instead of the cyclic peptide A was used, in "Preparation of cyclic peptide-immobilized carboxylated carrier—Introduction of cyclic peptide".

Lys-Lys-Lys-Asp-Xaa5-Ala-Tyr-His-Leu-Gly-Glu-
Leu-Val-Trp-Xaa15-Thr                 (B)

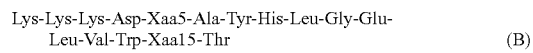

In the formula (B), any of Xaa5 and Xaa15 is an amino acid residue derived from L-homocysteine, and Xaa5 and Xaa15 form a disulfide bond between thiol groups of a side chain of L-homocysteine to crosslink thereof.

2. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.6 mmol/L-gel.

3. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

4. Evaluation of Antigenic Ligand Incorporation

Antigenic ligand incorporation of the obtained cyclic peptide-immobilized carboxylated carrier was evaluated by the above-described "Evaluation method of antigenic ligand incorporation". As a result, evaluation of the antigenic ligand incorporation was "A".

Example 3

1. Production of Mixed Mode Affinity Chromatography Carrier

A carboxylated carrier was prepared in the same manner as that of Example 1, except that the amount of sodium chloroacetate was changed to 6.1 g, in "Preparation of carboxylated carrier—Introduction of cation exchange group".

In addition, a cyclic peptide-immobilized carboxylated carrier was prepared in the same manner as that of Example 1, except that the carboxylated carrier prepared as described above was used and the cyclic peptide represented by the formula (C) (SEQ ID NO: 15) instead of the cyclic peptide A was used, in "Preparation of cyclic peptide-immobilized carboxylated carrier—Introduction of cyclic peptide".

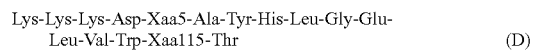

In the formula (C), Xaa5 is an amino acid residue derived from N-ε-chloroacetyl-L-lysine, Xaa15 is an amino acid residue derived from L-penicillamine, and Xaa5 and Xaa15 form a thioether bond between a chloroacetyl group of a side chain of N-ε-chloroacetyl-L-lysine and a thiol group of a side chain of L-penicillamine to crosslink thereof.

2. Measurement of Carboxy Group Introduction Amount

A carboxy group introduction amount of the obtained carboxylated carrier was measured by the above-described "Measurement method of cation exchange group introduction amount". As a result, the carboxy group introduction amount was 36 mmol/L-gel.

3. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 2.0 mmol/L-gel.

4. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

5. Evaluation of Antigenic Ligand Incorporation

Antigenic ligand incorporation of the obtained cyclic peptide-immobilized carboxylated carrier was evaluated based on the above-described "Evaluation method of antigenic ligand incorporation". As a result, evaluation of the antigenic ligand incorporation was "A".

Example 4

1. Production of Mixed Mode Affinity Chromatography Carrier

A cyclic peptide-immobilized carboxylated carrier was prepared in the same manner as that of Example 3, except that the carboxylated carrier prepared as described above was used and cyclic peptide D represented by the formula (D) (SEQ ID NO: 16) instead of the cyclic peptide A was used, in "Preparation of cyclic peptide-immobilized carboxylated carrier—Introduction of cyclic peptide".

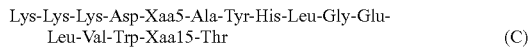

In the formula (D), Xaa5 is an amino acid residue derived from 2-propargyl-L-homoglycine, Xaa15 is an amino acid residue derived from f3-azide-L-alanine, and Xaa5 and Xaa15 form a triazole bond between a propargyl group of a side chain of 2-propargyl-L-homoglycine and an azide group of a side chain of 3-azide-L-alanine to crosslink thereof.

2. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.7 mmol/L-gel.

3. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

4. Evaluation of Antigenic Ligand Incorporation

Antigenic ligand incorporation of the obtained cyclic peptide-immobilized carboxylated carrier was evaluated by the above-described "Evaluation method of antigenic ligand incorporation". As a result, evaluation of the antigenic ligand incorporation was "A".

Example 5

1. Production of Mixed Mode Affinity Chromatography Carrier

A cyclic peptide-immobilized carboxylated carrier was prepared in the same manner as that of Example 3, except that the carboxylated carrier prepared as described above was used and cyclic peptide E represented by the formula (E) (SEQ ID NO: 17) instead of the cyclic peptide A was used, in "Preparation of cyclic peptide-immobilized carboxylated carrier—Introduction of cyclic peptide".

Lys-Lys-Lys-Asp-Xaa5-Ala-Tyr-His-Leu-Gly-Glu-Leu-Val-Trp-Xaa15-Thr (E)

In the formula (E), Xaa5 is an amino acid residue derived from N-ε-chloroacetyl-L-lysine, Xaa15 is an amino acid residue derived from cysteine, and Xaa5 and Xaa15 form a thioether bond between a chloroacetyl group of a side chain of N-ε-chloroacetyl-L-lysine, and a thiol group of a side chain of cysteine to crosslink thereof.

2. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.9 mmol/L-gel.

3. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

4. Evaluation of Antigenic Ligand Incorporation

Antigenic ligand incorporation of the obtained cyclic peptide-immobilized carboxylated carrier was evaluated by the above-described "Evaluation method of antigenic ligand incorporation". As a result, evaluation of the antigenic ligand incorporation was "A".

Example 6

1. Production of Mixed Mode Affinity Chromatography Carrier

A cyclic peptide-immobilized carboxylated carrier was prepared in the same manner as that of Example 1, except that cyclic peptide F represented by the formula (F) (SEQ ID NO: 18) instead of the cyclic peptide A was used, in "Preparation of cyclic peptide-immobilized carboxylated carrier—Introduction of cyclic peptide".

Lys-Lys-Lys-Asp-Xaa5-Ala-Tyr-His-Leu-Gly-Glu-Leu-Val-Trp-Xaa15-Thr (F)

In the formula (F), any of Xaa5 and Xaa15 is an amino acid residue derived from L-cysteine, and Xaa5 and Xaa15 form a disulfide bond between thiol groups of a side chain of L-cysteine to crosslink thereof.

2. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.8 mmol/L-gel.

3. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

4. Evaluation of Antigenic Ligand Incorporation

Antigenic ligand incorporation of the obtained cyclic peptide-immobilized carboxylated carrier was evaluated by the above-described "Evaluation method of antigenic ligand incorporation". As a result, evaluation of the antigenic ligand incorporation was "A".

Example 7

1. Production of Mixed Mode Affinity Chromatography Carrier

A cyclic peptide-immobilized carboxylated carrier was prepared in the same manner as that of Example 3, except that the carboxylated carrier prepared as described above was used, and a 1.5 mL of 10 mg/mL cyclic peptide G solution prepared by dissolving cyclic peptide G represented by the formula (G) (SEQ ID NO: 19) in DMSO, instead of the 1.5 mL of 5 mg/mL cyclic peptide A solution, was used, in "Preparation of cyclic peptide-immobilized carboxylated carrier—Introduction of cyclic peptide".

Lys-Lys-Lys-Asp-Xaa5-Ala-Tyr-His-Leu-Gly-Glu-Leu-Val-Trp-Xaa15-Thr (G)

In the formula (G), Xaa5 is an amino acid residue derived from L-lysine, Xaa15 is an amino acid residue derived from L-glutamic acid, and Xaa5 and Xaa15 form an amide bond between an amino group of a side chain of L-lysine and a carboxy group of a side chain of L-glutamic acid to crosslink thereof.

2. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.2 mmol/L-gel.

3. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

4. Evaluation of Antigenic Ligand Incorporation

Antigenic ligand incorporation of the obtained cyclic peptide-immobilized carboxylated carrier was evaluated by the above-described "Evaluation method of antigenic ligand incorporation". As a result, evaluation of the antigenic ligand incorporation was "A".

Comparative Example 1

1. Production of Mixed Mode Affinity Chromatography Carrier (1) Preparation of Wet Gel The crosslinked agarose-based substrate, Sepharose 4 Fast Flow (manufactured by GE Healthcare GmbH) was washed on a glass filter by repeating suspension and filtration using pure water, thereby obtaining a substrate slurry. The pure water was removed from the substrate slurry by suction filtration to obtain a wet gel.

(2) Preparation of Carboxylated Carrier—Introduction of Cation Exchange Group 15 g of the obtained wet gel, 11.7 g of sodium chloroacetate, and 31 mL of pure water were placed in a 100 mL three-neck flask and stirring of the contents of the flask was started in a warm bath at 50° C. After dissolution, 11 g of a 50% (w/w) aqueous sodium hydroxide solution was added dropwise in the flask over 1 hour in a warm bath at 50° C. while maintaining the temperature in the flask at about 50° C. After the whole amount of the aqueous sodium hydroxide solution was added dropwise, the mixed solution was further reacted for 3 hours and washed on a glass filter by repeating suspension and filtration using pure water to obtain a wet gel of the carboxylated carrier.

(3) Preparation of Cyclic Peptide-Immobilized Carboxylated Carrier—Introduction of Cyclic Peptide A cyclic peptide-immobilized carboxylated carrier was prepared in the same manner as that of Example 6, except that the carboxylated carrier prepared as described above was used.

2. Measurement of Carboxy Group Introduction Amount

The carboxy group introduction amount of the obtained carboxylated carrier was measured by the above-described "Measurement method of cation exchange group introduction amount". As a result, the carboxy group introduction amount was 26 mmol/L-gel.

3. Measurement of Cyclic Peptide Immobilization Amount

A cyclic peptide immobilization amount (affinity ligand introduction amount) of the obtained cyclic peptide-immobilized carboxylated carrier was measured by the above-described "Measurement method of affinity ligand introduction amount (peptide immobilization amount)". As a result, the cyclic peptide immobilization amount was 1.1 mmol/L-gel.

4. Evaluation of Antibody Adsorption Capacity, Impurities Removal Function, and Drug Resistance Antibody adsorption capacity, impurities removal function, and drug resistance of the obtained cyclic peptide-immobilized carboxylated carrier were evaluated in the same manner as that of Example 1. The evaluation results are respectively shown in the sections "Antibody adsorption capacity", "Impurities removal function", and "Drug resistance" in Table 3.

5. Evaluation of Antigenic Ligand Incorporation

Antigenic ligand incorporation of the obtained cyclic peptide-immobilized carboxylated carrier was evaluated by the above-described "Evaluation method of antigenic ligand incorporation". As a result, evaluation of the antigenic ligand incorporation was "A".

Comparative Example 2

1. Production of Mixed Mode Affinity Chromatography Carrier

A straight chain peptide-immobilized carboxylated carrier was prepared in the same manner as that of Example 3, except that the carboxylated carrier prepared as described above was used, and a 1.5 mL of 10 mg/mL straight chain peptide H solution prepared by dissolving a straight chain peptide H represented by the following formula (H) (SEQ ID NO: 20) in a 50 mM sodium hydrogen carbonate buffer, instead of the 1.5 mL of 5 mg/mL cyclic peptide A solution, was used, in "Preparation of cyclic peptide-immobilized carboxylated carrier—Introduction of cyclic peptide".

Lys-Lys-Lys-Lys-Lys-Glu-Gln-Gln-Asn-Ala-Phe-Tyr-
Glu-Ile-Leu-His-Leu-Pro-Asn-Leu-Thr-Glu-Glu-
Gln-Arg-Asn-Ala-Phe-Ile-Gln-Ser-Leu-Arg-Asp     (H)

2. Measurement of Straight Chain Peptide-Immobilization Amount

The straight chain peptide immobilization amount (affinity ligand introduction amount) of the obtained straight chain peptide-immobilized carboxylated carrier was measured by the above-described "Measurement method of affinity ligand introduction amount (peptide immobilization amount)". As a result, the straight chain peptide immobilization amount was 4.6 mmol/L-gel.

3. Evaluation of Antibody Adsorption Capacity, Impurities Removal Function, and Drug Resistance Antibody adsorption capacity, impurities removal function, and drug resistance of the obtained straight chain peptide-immobilized carboxylated carrier were evaluated in the same manner as that of Example 1. The evaluation results are respectively shown in the sections "Antibody adsorption capacity", "Impurities removal function", and "Drug resistance" in Table 3.

4. Evaluation of Antigenic Ligand Incorporation

Antigenic ligand incorporation of the obtained straight chain peptide-immobilized carboxylated carrier was evaluated by the above-described "Evaluation method of antigenic ligand incorporation". As a result, evaluation of the antigenic ligand incorporation was "B".

TABLE 3

|  | Substrate | Hydrophilic polymer | Affinity ligand | Cation exchange group | Antibody adsorption capacity | Impurities removal function | Drug resistance |
|---|---|---|---|---|---|---|---|
| Example 1 | Polysaccharides (4% agarose) | Present | Cyclic peptide A (Hcy-Lys thioether bond) | Present | A | A | AAA |
| Example 2 | Polysaccharides (4% agarose) | Present | Cyclic pepiide B (Hcy-Hcy disulfide bond) | Present | A | A | AAA |
| Example 3 | Polysaccharides (4% agarose) | Present | Cyclic peptide C (Pen-Lys thioether bond) | Present | A | A | AA |
| Example 4 | Polysaccharides (4% agarose) | Present | Cyclic peptide D (triazole bond) | Present | A | A | A |
| Example 5 | Polysaccharides (4% agarose) | Present | Cyclic peptide E (Cys-Lys thioether bond) | Present | A | A | A |
| Example 6 | Polysaccharides (4% agarose) | Present | Cyclic peptide F (Cys-Cys disulfide bond) | Present | A | B | B |
| Example 7 | Polysaccharides (4% agarose) | Present | Cyclic peptide G (amide bond) | Present | B | A | A |
| Comparative Example 1 | Polysaccharides (4% agarose) | Absent | Cyclic peptide F (Cys-Cys disulfide bond) | Present | A | E | B |

TABLE 3-continued

| | Substrate | Hydrophilic polymer | Affinity ligand | Cation exchange group | Antibody adsorption capacity | Impurities removal function | Drug resistance |
|---|---|---|---|---|---|---|---|
| Comparative Example 2 | Polysaccharides (4% agarose) | Present | Straight chain peptide H | Present | E | B | E |

<Explanation of Results>
(Antibody Adsorption Capacity)

Each of the mixed mode affinity chromatography carriers of Examples 1 to 7 was evaluated as having antibody adsorption capacity of "A" or "B", and exhibited sufficient antibody adsorption capacity.

In addition, the mixed mode affinity chromatography carrier of Comparative Example 1 was also evaluated as having antibody adsorption capacity of "A", and exhibited sufficient antibody adsorption capacity. It is considered that the reason why this result is caused is that a cyclic peptide was used as an affinity ligand.

On the other hand, although both the mixed mode affinity chromatography carriers of Examples 1 to 7 and the mixed mode affinity chromatography carrier of Comparative Example 2 include a hydrophilic polymer, the former was evaluated as having antibody adsorption capacity of "A" or "B", and the latter was evaluated as having antibody adsorption capacity of "E" and did not have sufficient antibody adsorption capacity. It is considered that the reason is that in the former, the affinity ligand is a cyclic peptide whereas in the latter, the affinity ligand is a straight chain peptide, and thus combination between the straight chain peptide and the hydrophilic polymer was not good. However, the mechanisms of different antibody adsorption capacities cannot be clearly explained at the present time.

(Impurities Removal Function)

Any of the mixed mode affinity chromatography carriers of Examples 1 to 7 were evaluated as having impurities removal function of "A" or "B" and had sufficient impurities removal function.

With respect to this, the mixed mode affinity chromatography carrier of Comparative Example 1 not including a hydrophilic polymer was evaluated as having impurities removal function of "E" and did not have sufficient impurities removal function.

On the other hand, the mixed mode affinity chromatography carrier of Comparative Example 2 including a hydrophilic polymer was evaluated as having impurities removal function of "B" and had sufficient impurities removal function.

It is considered that the result is obtained by the improvement in impurities removal function due to coexistence of the hydrophilic polymer and the cation exchange group.

(Drug Resistance)

The mixed mode affinity chromatography carriers of Examples 1 to 7 and Comparative Example 1 were evaluated as having drug resistance of "'B'" or higher and had sufficient drug resistance.

With respect to this, the mixed mode affinity chromatography carrier of Comparative Example 2 using a straight chain peptide as an affinity ligand was evaluated as having drug resistance of "E" and did not have sufficient drug resistance.

It is considered that the reason why this result is caused is that the straight chain peptide is inferior to the cyclic peptide in terms of drug resistance.

In addition, among Examples 1 to 7 and Comparative Example 1, Examples 1 and 2 were evaluated as having drug resistance of "AAA" and had particularly excellent drug resistance. From a viewpoint of drug resistance, as a cross-linked structure of the cyclic peptide, a thioether bond between a homocysteine residue and a haloacetyl group-containing amino acid residue (amino acid residue having a haloacetyl group in a side chain) and a disulfide bond between homocysteine residues are particularly preferable, a thioether bond between a penicillamine residue and a haloacetyl group-containing amino acid residue is secondly preferable, and a thioether bond between cysteine- and haloacetyl group-containing amino acid residues, a triazole bond, and an amide bond are next preferable to the secondly preferable one.

(Overview)

The mixed mode affinity chromatography carrier of the present invention comprises all of a substrate, a hydrophilic polymer, an antibody-binding cyclic peptide, and a cation exchange group, and thus are excellent in all of antibody adsorption capacity, impurities removal function, and drug resistance.

What is claimed is:

1. A mixed mode affinity chromatography carrier, comprising:
   a substrate that is at least one selected from the group consisting of a polysaccharide, an acrylate-based polymer, a methacrylate-based polymer, and a styrene-based polymer;
   a hydrophilic polymer coated on the substrate, the hydrophilic polymer being a hydrophilic polysaccharide;
   an antibody-binding cyclic peptide that includes a cyclic portion cyclized by intramolecular crosslinking between side chains; and
   a cation exchange group that is a carboxy group or a sulfoxy group.

2. The mixed mode affinity chromatography carrier according to claim 1,
   wherein the intramolecular crosslinking includes at least one selected from the group consisting of a disulfide bond, a thioether bond, a triazole bond, and an amide bond.

3. The mixed mode affinity chromatography carrier according to claim 1,
   wherein the intramolecular crosslinking includes at least one selected from the group consisting of a disulfide bond, a thioether bond, and a triazole bond.

4. The mixed mode affinity chromatography carrier according to claim 3,
   wherein the disulfide bond is a disulfide bond formed between a side chain thiol group of a first amino acid residue derived from an amino acid having a thiol group in a side chain other than L-cysteine and D-cysteine and a side chain thiol group of a second amino acid residue derived from an amino acid having a thiol group in a side chain other than L-cysteine and D-cysteine, and
   wherein the thioether bond is a thioether bond formed between a side chain thiol group of a first amino acid residue derived from an amino acid having a thiol group in a side chain other than L-cysteine and D-cysteine and a side chain haloacetyl group of a second amino acid residue derived from an amino acid having a haloacetyl group in a side chain.

5. The mixed mode affinity chromatography carrier according to claim 3,
   wherein the disulfide bond is a disulfide bond formed between a side chain thiol group of a first amino acid residue derived from an amino acid having a thiol group in a side chain selected from the group consisting of cysteine, homocysteine, and penicillamine and a side chain thiol group of a second amino acid residue derived from an amino acid having a thiol group in a side chain selected from the group consisting of cysteine, homocysteine, and penicillamine, and wherein the thioether bond is a thioether bond formed between a side chain thiol group of a first amino acid residue derived from an amino acid having a thiol group in a side chain selected from the group consisting of cysteine, homocysteine, and penicillamine and a side chain haloacetyl group of a second amino acid residue derived from an amino acid having a haloacetyl group in a side chain.

6. The mixed mode affinity chromatography carrier according to claim 3,
wherein the disulfide bond is a disulfide bond formed between a side chain thiol group of a first amino acid residue derived from an amino acid having a thiol group in a side chain selected from the group consisting of homocysteine and penicillamine and a side chain thiol group of a second amino acid residue derived from an amino acid having a thiol group in a side chain selected from the group consisting of homocysteine and penicillamine, and
wherein the thioether bond is a thioether bond formed between a side chain thiol group of a first amino acid residue derived from an amino acid having a thiol group in a side chain selected from the group consisting of homocysteine and penicillamine and a side chain haloacetyl group of a second amino acid residue derived from an amino acid having a haloacetyl group in a side chain.

7. The mixed mode affinity chromatography carrier according to claim 1,
wherein the intramolecular crosslinking is a disulfide bond formed between a side chain thiol group of a first amino acid residue derived from an amino acid having a thiol group in a side chain selected from the group consisting of homocysteine and penicillamine and a side chain thiol group of a second amino acid residue derived from an amino acid having a thiol group in a side chain selected from the group consisting of homocysteine and penicillamine, or a thioether bond formed between a side chain thiol group of a first amino acid residue derived from an amino acid having a thiol group in a side chain selected from the group consisting of homocysteine and penicillamine and a side chain haloacetyl group of a second amino acid residue derived from an amino acid having a haloacetyl group in a side chain.

8. The mixed mode affinity chromatography carrier according to claim 7,
wherein the disulfide bond is a disulfide bond formed between a side chain thiol group of a first amino acid residue derived from homocysteine and a side chain thiol group of a second amino acid residue derived from homocysteine, and
wherein the thioether bond is a thioether bond formed between a side chain thiol group of a first amino acid residue derived from homocysteine and a side chain haloacetyl group of a second amino acid residue derived from an amino acid having a haloacetyl group in a side chain.

9. The mixed mode affinity chromatography carrier according to claim 1,
wherein the number of the amino acid residues of the cyclic portion is 8 to 14.

10. The mixed mode affinity chromatography carrier according to claim 1,
wherein the antibody-binding cyclic peptide includes a straight chain portion.

11. The mixed mode affinity chromatography carrier according to claim 10,
wherein the straight chain portion includes an amino acid residue having at least one selected from the group consisting of a hydroxy group and a carboxy group in a side chain.

12. The mixed mode affinity chromatography carrier according to claim 1,
wherein the substrate is at least one selected from the group consisting of a polysaccharide, an acrylate-based polymer, and a methacrylate-based polymer.

13. The mixed mode affinity chromatography carrier according to claim 1,
wherein the substrate is at least one selected from the group consisting of agarose and cellulose.

14. The mixed mode affinity chromatography carrier according to claim 1,
wherein the hydrophilic polysaccharide is at least one selected from the group consisting of dextran, carboxymethyl dextran, pullulan, hydroxyethyl cellulose, and carboxymethyl cellulose.

15. The mixed mode affinity chromatography carrier according to claim 1,
wherein the hydrophilic polysaccharide is at least one selected from the group consisting of dextran, carboxymethyl dextran, and pullulan.

16. The mixed mode affinity chromatography carrier according to claim 1,
wherein the cation exchange group is a carboxy group.

17. A mixed mode affinity chromatography carrier, comprising:
a substrate that is at least one selected from the group consisting of a polysaccharide, an acrylate-based polymer, a methacrylate-based polymer, and a styrene-based polymer;
a hydrophilic polymer that is a hydrophilic polysaccharide;
an antibody-binding cyclic peptide that includes a cyclic portion cyclized by intramolecular crosslinking between side chains; and
a cation exchange group that is a carboxy group or a sulfoxy group,
wherein the intramolecular crosslinking includes at least one selected from the group consisting of a disulfide bond, a thioether bond, and a triazole bond,
the disulfide bond is a disulfide bond formed between a side chain thiol group of a first amino acid residue derived from an amino acid having a thiol group in a side chain other than L-cysteine and D-cysteine and a side chain thiol group of a second amino acid residue derived from an amino acid having a thiol group in a side chain other than L-cysteine and D-cysteine, and
wherein the thioether bond is a thioether bond formed between a side chain thiol group of a first amino acid residue derived from an amino acid having a thiol group in a side chain other than L-cysteine and D-cysteine and a side chain haloacetyl group of a second amino acid residue derived from an amino acid having a haloacetyl group in a side chain.

18. A mixed mode affinity chromatography carrier, comprising:
a substrate that is at least one selected from the group consisting of a polysaccharide, an acrylate-based polymer, a methacrylate-based polymer, and a styrene-based polymer;
a hydrophilic polymer that is a hydrophilic polysaccharide;

an antibody-binding cyclic peptide that includes a cyclic portion cyclized by intramolecular crosslinking between side chains; and a cation exchange group that is a carboxy group or a sulfoxy group, wherein the intramolecular crosslinking includes at least one selected from the group consisting of a disulfide bond, a thioether bond, and a triazole bond, wherein the disulfide bond is a disulfide bond formed between a side chain thiol group of a first amino acid residue derived from an amino acid having a thiol group in a side chain selected from the group consisting of cysteine, homocysteine, and penicillamine and a side chain thiol group of a second amino acid residue derived from an amino acid having a thiol group in a side chain selected from the group consisting of cysteine, homocysteine, and penicillamine, and wherein the thioether bond is a thioether bond formed between a side chain thiol group of a first amino acid residue derived from an amino acid having a thiol group in a side chain selected from the group consisting of cysteine, homocysteine, and penicillamine and a side chain haloacetyl group of a second amino acid residue derived from an amino acid having a haloacetyl group in a side chain.

* * * * *

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Ala Tyr His Leu Gly Glu Leu Val Trp
1               5

<210> SEQ ID NO 2
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 2

Ala Tyr His Arg Gly Glu Leu Val Trp
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide, ring_part_1
<220> FEATURE:
<221> NAME/KEY: MISC_FEATURE
<222> LOCATION: (1)..(11)
<223> OTHER INFORMATION: Xaa1 is an amino acid residue derived from
      L-homocysteine. Xaa11 is an amino acid residue derived from
      N-epsilon-chloroacetyl-L-lysine. Xaa1 and Xaa11 are briged by a
      thioether bond.

<400> SEQUENCE: 3

Xaa Ala Tyr His Leu Gly Glu Leu Val Trp Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide, ring_part_2
<220> FEATURE:
<221> NAME/KEY: MISC_FEATURE
<222> LOCATION: (1)..(11)
<223> OTHER INFORMATION: Xaa1 is an amino acid residue derived from
      N-epsilon-chloroacetyl-L-lysine. Xaa11 is an amino acid residue
      derived from L-homocysteine. Xaa1 and Xaa11 are briged by a
      thioether bond.

<400> SEQUENCE: 4

Xaa Ala Tyr His Leu Gly Glu Leu Val Trp Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide, ring_part_3
<220> FEATURE:
<221> NAME/KEY: MISC_FEATURE
<222> LOCATION: (1)..(11)
<223> OTHER INFORMATION: Xaa1 is an amino acid residue derived from
      L-cysteine. Xaa11 is an amino acid residue derived from
      N-epsilon-chloroacetyl-L-lysine. Xaa1 and Xaa11 are briged by a
      thioether bond.

<400> SEQUENCE: 5

Xaa Ala Tyr His Leu Gly Glu Leu Val Trp Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide, ring_part_4
<220> FEATURE:
<221> NAME/KEY: MISC_FEATURE
```

```
<222> LOCATION: (1)..(11)
<223> OTHER INFORMATION: Xaa1 is an amino acid residue derived from
      N-epsilon-chloroacetyl-L-lysine. Xaa11 is an amino acid residue
      derived from L-penicillamine. Xaa1 and Xaa11 are briged by a
      thioether bond.

<400> SEQUENCE: 6

Xaa Ala Tyr His Leu Gly Glu Leu Val Trp Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide, ring_part-5:
      -
-A-Y-H-L-G-E-L-V-W-(Lys(Ac)
- Hcy is an amino acid residue
      induced from homocysteine. Lys(Ac) is an amino acid residue
      induced from N-epsilon-chloroacetyl-L-lysine.
<220> FEATURE:
<221> NAME/KEY: MISC_FEATURE
<222> LOCATION: (1)..(11)
<223> OTHER INFORMATION: Xaa1 and Xaa11 are amino acid residues derived
      from L-homocysteine. Xaa1 and Xaa11 are bridged by a disulfide
      bond.

<400> SEQUENCE: 7

Xaa Ala Tyr His Leu Gly Glu Leu Val Trp Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide, ring_part_6
<220> FEATURE:
<221> NAME/KEY: MISC_FEATURE
<222> LOCATION: (1)..(11)
<223> OTHER INFORMATION: Xaa1 and Xaa11 are amino acid residues derived
      from L-penicillamine. Xaa1 and Xaa11 are bridged by a disulfide
      bond.

<400> SEQUENCE: 8

Xaa Ala Tyr His Leu Gly Glu Leu Val Trp Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide, ring_part_7
<220> FEATURE:
<221> NAME/KEY: MISC_FEATURE
<222> LOCATION: (1)..(11)
<223> OTHER INFORMATION: Xaa1 is an amino acid residue derived from
      2-propargyl-L-homoglycine. Xaa11 is an amino acid residue derived
      from beta-azido-L-alanine.

<400> SEQUENCE: 9

Xaa Ala Tyr His Leu Gly Glu Leu Val Trp Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide, ring_part_8
```

```
<220> FEATURE:
<221> NAME/KEY: MISC_FEATURE
<222> LOCATION: (1)..(11)
<223> OTHER INFORMATION: Xaa1 is an amino acid residue derived from
      beta-azido-L-alanine. Xaa11 is an amino acid residue derived from
      2-propargyl-L-homoglycine. Xaa1 and Xaa11 are briged by a
      triazole bond.

<400> SEQUENCE: 10

Xaa Ala Tyr His Leu Gly Glu Leu Val Trp Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide, ring_part_9
<220> FEATURE:
<221> NAME/KEY: MISC_FEATURE
<222> LOCATION: (1)..(11)
<223> OTHER INFORMATION: Xaa1 is an amino acid residue derived from
      L-lysine. Xaa11 is an amino acid residue derived from L-glutamic
      acid. Xaa1 and Xaa11 are briged by an amide bond.

<400> SEQUENCE: 11

Xaa Ala Tyr His Leu Gly Glu Leu Val Trp Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide, ring_part_10
<220> FEATURE:
<221> NAME/KEY: MISC_FEATURE
<222> LOCATION: (1)..(11)
<223> OTHER INFORMATION: Xaa1 is an amino acid residue derived from
      L-glutamic acid. Xaa11 is an amino acid residue derived from
      L-lysine. Xaa1 and Xaa11 are briged by an amide bond.

<400> SEQUENCE: 12

Xaa Ala Tyr His Leu Gly Glu Leu Val Trp Xaa
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide, cyclic_peptide-A
<220> FEATURE:
<221> NAME/KEY: MISC_FEATURE
<222> LOCATION: (5)..(15)
<223> OTHER INFORMATION: Xaa5 is an amino acid residue derived from
      N-epsilon-chloroacetyl-L-lysine. Xaa15 is an amino acid residue
      derived from L-homocysteine. Xaa5 and Xaa15 are briged by a
      thioether bond.

<400> SEQUENCE: 13

Lys Lys Lys Asp Xaa Ala Tyr His Leu Gly Glu Leu Val Trp Xaa Thr
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide, cyclic_peptide-B
<220> FEATURE:
```

```
<221> NAME/KEY: MISC_FEATURE
<222> LOCATION: (5)..(15)
<223> OTHER INFORMATION: Xaa5 and Xaa15 are amino acid residues derived
      from L-homocysteine. Xaa5 and Xaa15 are bridged by a disulfide
      bond.

<400> SEQUENCE: 14

Lys Lys Lys Asp Xaa Ala Tyr His Leu Gly Glu Leu Val Trp Xaa Thr
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide, cyclic_peptide-C
<220> FEATURE:
<221> NAME/KEY: MISC_FEATURE
<222> LOCATION: (5)..(15)
<223> OTHER INFORMATION: Xaa5 is an amino acid residue derived from
      N-epsilon-chloroacetyl-L-lysine. Xaa15 is an amino acid residue
      derived from L-penicillamine. Xaa5 and Xaa15 are briged by a
      thioether bond.

<400> SEQUENCE: 15

Lys Lys Lys Asp Xaa Ala Tyr His Leu Gly Glu Leu Val Trp Xaa Thr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide, cyclic_peptide-D
<220> FEATURE:
<221> NAME/KEY: MISC_FEATURE
<222> LOCATION: (5)..(15)
<223> OTHER INFORMATION: Xaa5 is an amino acid residue derived from
      2-propargyl-L-homoglycine. Xaa15 is an amino acid residue derived
      from beta-azido-L-alanine.

<400> SEQUENCE: 16

Lys Lys Lys Asp Xaa Ala Tyr His Leu Gly Glu Leu Val Trp Xaa Thr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide, cyclic_peptide-E
<220> FEATURE:
<221> NAME/KEY: MISC_FEATURE
<222> LOCATION: (5)..(15)
<223> OTHER INFORMATION: Xaa5 is an amino acid residue derived from
      N-epsilon-chloroacetyl-L-lysine. Xaa15 is an amino acid residue
      derived from L-cysteine. Xaa5 and Xaa15 are briged by a thioether
      bond.

<400> SEQUENCE: 17

Lys Lys Lys Asp Xaa Ala Tyr His Leu Gly Glu Leu Val Trp Xaa Thr
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide, cyclic_peptide-F
<220> FEATURE:
<221> NAME/KEY: MISC_FEATURE
```

```
<222> LOCATION: (5)..(15)
<223> OTHER INFORMATION: Xaa5 and Xaa15 are amino acid residues derived
      from L-cysteine. Xaa5 and Xaa15 are bridged by a disulfide bond.

<400> SEQUENCE: 18

Lys Lys Lys Asp Xaa Ala Tyr His Leu Gly Glu Leu Val Trp Xaa Thr
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide, cyclic_peptide-G
<220> FEATURE:
<221> NAME/KEY: MISC_FEATURE
<222> LOCATION: (5)..(15)
<223> OTHER INFORMATION: Xaa5 is an amino acid residue derived from
      L-lysine. Xaa15 is an amino acid residue derived from L-glutamic
      acid. Xaa5 and Xaa15 are briged by an amide bond.

<400> SEQUENCE: 19

Lys Lys Lys Asp Xaa Ala Tyr His Leu Gly Glu Leu Val Trp Xaa Thr
1               5                   10                  15

<210> SEQ ID NO 20
<211> LENGTH: 34
<212> TYPE: PRT
<213> ORGANISM: Artificial Sequence
<220> FEATURE:
<223> OTHER INFORMATION: Synthetic peptide, linear_peptide-H

<400> SEQUENCE: 20

Lys Lys Lys Lys Lys Glu Gln Gln Asn Ala Phe Tyr Glu Ile Leu His
1               5                   10                  15

Leu Pro Asn Leu Thr Glu Glu Gln Arg Asn Ala Phe Ile Gln Ser Leu
            20                  25                  30

Arg Asp
```